(12) United States Patent
Messersmith et al.

(10) Patent No.: US 9,259,473 B2
(45) Date of Patent: Feb. 16, 2016

(54) POLYMER HYDROGEL ADHESIVES FORMED WITH MULTIPLE CROSSLINKING MECHANISMS AT PHYSIOLOGIC PH

(71) Applicants: Phillip B. Messersmith, Clarendon Hills, IL (US); Devin G. Barrett, Evanston, IL (US); Iossif A. Strehin, Evanston, IL (US)

(72) Inventors: Phillip B. Messersmith, Clarendon Hills, IL (US); Devin G. Barrett, Evanston, IL (US); Iossif A. Strehin, Evanston, IL (US)

(73) Assignee: Northwestern University, Evanston, IL (US)

( * ) Notice: Subject to any disclaimer, the term of this patent is extended or adjusted under 35 U.S.C. 154(b) by 356 days.

(21) Appl. No.: 13/798,744

(22) Filed: Mar. 13, 2013

(65) Prior Publication Data

US 2013/0345319 A1 Dec. 26, 2013

Related U.S. Application Data

(60) Provisional application No. 61/662,563, filed on Jun. 21, 2012.

(51) Int. Cl.
| | | |
|---|---|---|
| *A61K 47/34* | (2006.01) | |
| *A61L 24/00* | (2006.01) | |
| *C08J 3/075* | (2006.01) | |
| *A61L 24/04* | (2006.01) | |
| *C08J 3/24* | (2006.01) | |

(52) U.S. Cl.
CPC .............. *A61K 47/34* (2013.01); *A61L 24/0031* (2013.01); *A61L 24/046* (2013.01); *C08J 3/075* (2013.01); *C08J 3/246* (2013.01); *C08J 2371/02* (2013.01)

(58) Field of Classification Search
CPC ..... A61L 31/06; A61L 2400/18; A61L 27/52; A61L 27/58; A61L 31/14
See application file for complete search history.

(56) References Cited

U.S. PATENT DOCUMENTS

| | | | |
|---|---|---|---|
| 2006/0009550 A1* | 1/2006 | Messersmith et al. | 524/17 |
| 2008/0220047 A1* | 9/2008 | Sawhney et al. | 424/426 |
| 2008/0247984 A1 | 10/2008 | Messersmith | |
| 2011/0189290 A1 | 8/2011 | Sundaram | |
| 2011/0262492 A1 | 10/2011 | Messersmith | |

FOREIGN PATENT DOCUMENTS

| | | | | |
|---|---|---|---|---|
| CN | 102206409 | * | 10/2011 | 424/401 |
| CN | 102206409 A | | 10/2011 | |
| WO | 0033764 A1 | | 6/2000 | |
| WO | 0062827 A2 | | 10/2000 | |
| WO | 20080131325 A2 | | 10/2008 | |
| WO | 20110084710 A1 | | 7/2011 | |

OTHER PUBLICATIONS

CN102206409A, published Oct. 5, 2011 to Tianzhu, translation.*
PCT International Preliminary Report on Patentability, PCT/US2013/030928, Dec. 23, 2014, 6 pages.
PCT International Search Report and Written Opinion, PCT/US2013/030928 May 23, 2013.

* cited by examiner

*Primary Examiner* — Audrea Buckley
(74) *Attorney, Agent, or Firm* — Quarles & Brady, LLP

(57) ABSTRACT

The present invention encompasses biocompatible reactants, biocompatible product hydrogels, methods of use thereof, and methods of synthesis thereof using a novel crosslinking mechanism between a first reactant compound including an N-Hydroxysuccinimide (NHS) ester group and a second reactant compound including a N-terminal cysteine amine group. In certain embodiments, one or more of the reactant compounds may be a macromonomer.

11 Claims, 26 Drawing Sheets

Native Chemical Ligation (NCL)

Oxoester Mediated Native Chemical Ligation (OMNCL)

A

B

C

D

E

F

POLYMER HYDROGEL ADHESIVES FORMED WITH MULTIPLE CROSSLINKING MECHANISMS AT PHYSIOLOGIC PH

CROSS-REFERENCE TO RELATED APPLICATIONS

This application claims priority to U.S. Provisional Appn. No. 61/662,563 filed Jun. 21, 2013, the entirety of which is hereby incorporated by reference in its entirety for all purposes.

STATEMENT REGARDING FEDERALLY-SPONSORED RESEARCH OR DEVELOPMENT

This invention was made with government support under R01 DE 021104 awarded by the National Institutes of Health. The government has certain rights in the invention.

FIELD OF THE INVENTION

This invention is directed to biocompatible hydrogel adhesives and methods of synthesizing such adhesives using a novel crosslinking mechanism.

BACKGROUND OF THE INVENTION

When first described in 1992,[1] native chemical ligation (NCL) revolutionized peptide synthesis by providing a facile, chemoselective synthetic method for preparation of large peptides and functional proteins from short fragments. In NCL, an unprotected N-terminal cysteine (Cys) of one peptide reacts with the thioester-activated C-terminus of another peptide to form a thioester intermediate that rearranges via an S-to-N acyl migration to yield an amide bond linking the two fragments together (FIG. 1).[2,3] NCL leads to minimal epimerization and byproduct formation and is highly selective to the N-terminal Cys, allowing the use of unprotected, post-translationally modified, and non-naturally occurring amino acids. NCL has been used to synthesize ion channel proteins such as KcsA,[4] the plant protein crambin,[3] glycosylated proteins such as monocyte chemotactic protein-3,[5] and other difficult or otherwise impossible protein sequences.

Several research groups in the biomaterials community have explored NCL for preparation of functional materials.[6-12] These studies focused on the use of NCL for synthesis of collagen mimetic biomaterials,[9] chemical modification of polymers[10,11] and self-assembled peptide scaffolds,[8] and modification of substrate surfaces.[6] In principle, the chemoselectivity of NCL is attractive for in vitro and in vivo use, allowing chemical reactions to proceed with specificity in a complex biological milieu, preserving the bioactivity of endogenous compounds and facilitating the targeting of therapeutic or diagnostic molecules to specific biomolecular targets such as cell surface proteins and components of the extracellular matrix. We have been developing polymer hydrogels cross-linked via NCL,[7,12] for potential in vitro and in vivo applications. The general strategy involves the reaction of a thioester-derivatized polymer with a second polymer containing N-terminal Cys residues. Mixing of the two polymer precursors under mild aqueous conditions led to gel network formation via NCL without the need for added catalysts.[7] Later, we extended this strategy to the formation of gels for in vitro cell encapsulation, incorporating polymer-bound IL-1 receptor inhibitory peptides that provided an immunoprotective effect to entrapped insulin secreting cells.[12]

Despite these recent advances, several aspects of the NCL reaction remain challenging for use in a biological setting. For example, standard NCL conditions employ the use of strong reducing agents that may be harmful in living systems. Furthermore, the slow rate of NCL cross-linking[7], the hydrolytic instability of the thioester, and the adverse biological effects of the thiol leaving group[13] remain obstacles to future in vivo applications of NCL.

Several modifications of the NCL reaction have been introduced in an effort to expand the utility of the method.[14-16] Danishefsky and coworkers described the use of oxo-esters in NCL (FIG. 1), first through an indirect approach involving o-thiophenolic ester[17] and followed later by a direct approach utilizing p-nitrophenyl (pNP) activated C-terminal ester.[18] Termed "oxo-ester-mediated NCL" (OMNCL), this approach enables high efficiency reactions even with bulky C-terminal amino acids, although disadvantages include hydrolytic susceptibility of the pNP ester and challenges associated with direct solid phase synthesis of pNP ester peptides.[19] Weissenborn et al. described OMNCL on oxo-ester activated surfaces and found 2,3,4,5,6-pentafluorophenyl (PFP) to be more efficient than pNP and N-hydroxysuccinimide (NHS) activating agents.[20]

Here we describe polymer hydrogel formation via OMNCL between branched polymer precursors containing NHS activated ester and N-Cys endgroups.[21] Mixing of NHS and N-Cys polymer precursors led to gel formation within seconds, and quantitative NMR studies revealed the crosslinking mechanism to be OMNCL. In addition to characterizing the bulk mechanical and adhesive properties of the hydrogels, we performed the first in vitro and in vivo studies of OMNCL hydrogels, showing favorable biological response in cytotoxicity assays and in a subcutaneous implant model. The OMNCL hydrogel strategy overcomes many of the earlier limitations of NCL, including cytotoxicity of thiol leaving groups and slow reaction kinetics, and represents a promising strategy for chemical cross-linking of hydrogels in a biological context.

Specifically, hydrogel materials are appealing as their high water content and efficient mass transfer are similar to that of native tissue. One current clinical use of hydrogels is as sealants since they decrease the incidence of reoperation due to surgical wound leaks and results in the decrease of cost and patient morbidity.[10] In addition, coating tissue surfaces with exogenous hydrogel materials may lead to the decrease in the incidence rate of tissue to tissue adhesion thus decreasing postoperative complications.[11,12] Therefore, tissue adhesive hydrogels are used daily by surgeons to circumvent complications and establish adequate wound closure. Some limitations attributed to the existing NCL hydrogels include slow reaction kinetics at physiological pH and some cytotoxicity associated with the release of small molecular weight thiol containing molecules.

Accordingly, there is a need for a tissue adhesive hydrogel formulation that uses a modification to the NCL chemistry that results in faster reaction times under physiological conditions and that produces a strong, non-cytotoxic product.

SUMMARY OF THE INVENTION

The present invention provides a hydrogel obtained by covalently cross-linking a first macromonomer comprising an N-Hydroxysuccinimide (NHS) ester group with a second macromonomer comprising a N-terminal cysteine group. In one embodiment, covalently cross-linking the first and second macromonomers comprises (a) forming an amide bond between the carboxyl carbon of the N-Hydroxysuccinimide (NHS) ester group of the first macromonomer and the primary amine of the terminal cysteine group of the second macromonomer to form a third macromonomer, and (b) forming a disulfide bond between primary thiol groups on two of the third macromonomers produced in step (a).

In one embodiment, the hydrogel is biocompatible and the first macromonomer, the second macromonomer, or both, comprise polyethylene glycol.

In one embodiment, the first macromonomer is selected from the group consisting of P8G-NHS, P8GG-NHS, P8MG-NHS, P8S-NHS, P8MS-NHS and T4G-NHS as set forth in FIG. 26.

In one embodiment, the second macromonomer comprises a catechol group such as P8Cys.

In one embodiment, each n has a value in the range of from 1 to 201, and wherein each R comprises a hexaglycerin core or a tripentaerythritol core.

The invention also provides a method of synthesizing a hydrogel comprising covalently cross-linking an effective amount of a first macromonomer comprising an N-Hydroxysuccinimide (NHS) ester group with an effective amount of a second macromonomer comprising a terminal cysteine group, wherein a hydrogel is formed. The step of covalently cross-linking the first and second macromonomers comprises: (a) forming an amide bond between the carboxyl carbon of the N-Hydroxysuccinimide (NHS) ester group of the first macromonomer and the primary amine of the terminal cysteine group of the second macromonomer to form a third macromonomer, and (b) forming a disulfide bond between primary thiol groups on two of the third macromonomers produced in step (a). The hydrogel formed is biocompatible and the step of covalently cross-linking the first and second macromonomers occurs at physiological pH.

In one embodiment, the first macromonomer, the second macromonomer, or both, comprise polyethylene glycol.

In one embodiment the first macromonomer is selected from the group consisting of P8G-NHS, P8GG-NHS, P8MG-NHS, P8S-NHS, P8MS-NHS and T4G-NHS as set forth in FIG. 26.

In one embodiment, the second macromonomer further comprises a catechol group and is P8Cys.

In one embodiment, each n has a value in the range of from 1 to 201, and wherein each R comprises a hexaglycerin core or a tripentaerythritol core.

The invention also provides a kit for synthesizing a biocompatible hydrogel comprising: (a) a first macromonomer comprising an N-Hydroxysuccinimide (NHS) ester group; and (b) a second macromonomer comprising a N-terminal cysteine group, wherein the first macromonomer, the second macromonomer, or both, comprise polyethylene glycol.

In one embodiment, the first macromonomer, the second macromonomer, or both, comprise polyethylene glycol.

In one embodiment the first macromonomer is selected from the group consisting of P8G-NHS, P8GG-NHS, P8MG-NHS, P8S-NHS, P8MS-NHS and T4G-NHS as set forth in FIG. 26.

In one embodiment, the second macromonomer is P8Cys.

While multiple embodiments are disclosed, still other embodiments of the present invention will become apparent to those skilled in the art from the following detailed description. As will be apparent, the invention is capable of modifications in various obvious aspects, all without departing from the spirit and scope of the present invention. Accordingly, the detailed descriptions are to be regarded as illustrative in nature and not restrictive.

DETAILED DESCRIPTION OF THE INVENTION

Figure 1:
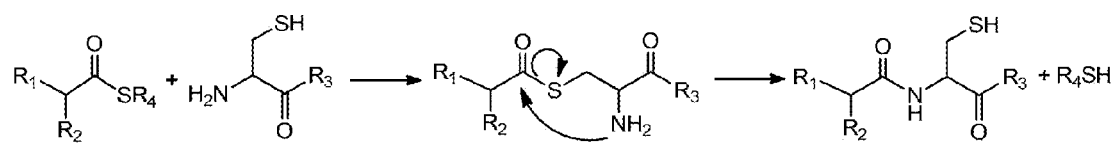
FIG. 1. Generalized reaction schemes for native chemical ligation (NCL) and oxo-ester mediated native chemical ligation (OMNCL).
Figure 1:
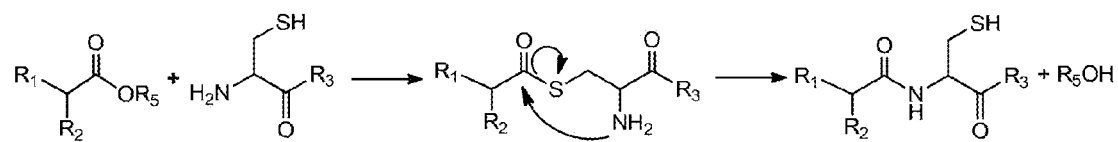

The present invention provides a new type of oxo-ester mediated native chemical ligation (OMNCL) for polymer hydrogel formation, in vitro cell encapsulation, and in vivo implantation. Multivalent polymer precursors containing N-hydroxysuccinimide (NHS)-activated oxo-esters and N-cysteine (N-Cys) endgroups were chemically synthesized from branched poly(ethylene glycol) (PEG). Hydrogels formed rapidly at physiologic pH upon mixing of aqueous solutions of NHS and N-Cys functionalized PEGs. the reaction proceeds through an OMNCL pathway involving thiol capture to form a thioester intermediate, followed by an S-to-N acyl rearrangement to yield an amide cross-link. pH and temperature were found to influence gelation rate, allowing tailoring of gelation times from a few seconds to a few minutes. OMNCL hydrogels initially swelled before contracting to reach an equilibrium increase in relative wet weight of 0%. This unique behavior impacted the gel stiffness and was attributed to latent formation of disulfide cross-links between network-bound Cys residues. OMNCL hydrogels were adhesive to hydrated tissue, generating a lap shear adhesion strength of 46 kPa. Cells encapsulated in OMNCL hydrogels maintained high viability, and in situ formation of OMNCL hydrogel by subcutaneous injection in mice generated a minimal acute inflammatory response. OMNCL represents a promising strategy for chemical cross-linking of hydrogels in a biological context and is an attractive candidate for in vivo applications such as wound healing, tissue repair, drug delivery, and tissue engineering.

The invention provides biocompatible reactant compounds, such as macromonomers having an NHS ester or cysteine group, methods of synthesis of such reactant compounds, methods of hydrogel formation by reaction of the NHS ester with the cysteine group, and methods of using such hydrogels.

IN GENERAL

In the specification and in the claims, the terms "including" and "comprising" are open-ended terms and should be interpreted to mean "including, but not limited to . . . ." These terms encompass the more restrictive terms "consisting essentially of" and "consisting of:"

As used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", "characterized by" and "having" can be used interchangeably.

Unless defined otherwise, all technical and scientific terms used herein have the same meanings as commonly understood by one of ordinary skill in the art to which this invention belongs. All publications and patents specifically mentioned herein are incorporated by reference in their entirety for all purposes including describing and disclosing the chemicals, instruments, statistical analyses and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

While multiple embodiments are disclosed, still other embodiments of the present invention will become apparent to those skilled in the art from the following detailed description. As will be apparent, the invention is capable of modifications in various obvious aspects, all without departing from the spirit and scope of the present invention. Accordingly, the detailed description of the hydrogels of the present invention are to be regarded as illustrative in nature and not restrictive.

THE INVENTION

The present invention encompasses biocompatible reactants, biocompatible hydrogels, methods of use thereof, and methods of synthesis thereof using a novel crosslinking mechanism between a first reactant compound including an N-Hydroxysuccinimide (NHS) ester group and a second reactant compound including a N-terminal cysteine amine group. In certain embodiments, one or more of the reactant compounds may be a macromonomer.

Two distinct crosslink types form between the first and second reactant compounds. First, upon initial reaction between the two compounds, a thioester bond is formed between the first and second compound. The proximity and orientation of the primary amine in relation to the thioester leads to a rearrangement to form a more stable and more permanent amide bond. The second crosslink is a disulfide bond that forms between the resulting products. Accordingly, the synthetic method encompasses a chemoselective reaction between a N-Hydroxysuccinimide (NHS) ester structure and a cysteine structure. The reaction proceed with a mechanism that is similar to the mechanism of native chemical ligation, where transthioesterification between the two reactants first gives a linked thioester-intermediate, and then this intermediate rearranges irreversibly under the usual reaction conditions to form a native amide ('peptide') bond at the ligation site.

The synthesis and use of specific reactant compounds and macromonomers that can be used in the synthetic method, as well as specific hydrogels made using these reactant compounds and macromonomers, are disclosed herein. At physiological pH, the disclosed method quickly produces strong, biocompatible and non-toxic hydrogels. Accordingly, the method can be used in making biomedical products, such as sutures and tissue replacement biomaterials, and for encapsulating therapeutic cells and pharmaceuticals.

Compared to the conventional native chemical ligation reaction, the use of an NHS ester in this reaction results in rapid formation of a conjugate product without the release of soluble thiol-containing molecules as side products. The resulting hydrogels have significantly increased biocompatibility compared to those formed from conventional thioester-conjugated macromonomers through the native chemical ligation mechanism. We envision that the disclosed novel conjugation strategy, the disclosed reactant compounds and macromonomers containing the NHS esters, and methods of hydrogel formation using NHS esters will have wide-ranging utility in both basic and applied biomedical applications.

Accordingly, the invention encompasses the use of the methods disclosed herein in the development of biomedical products, such as surgical sutures, tissue replacement materials and materials for the encapsulation of therapeutic cells and pharmaceuticals. In one embodiment, this aspect includes a method of encapsulating a biological sample with biomaterials. The method is carried out by a) preparing a biocompatible hydrogel according to the disclosed method, reacting the biocompatible hydrogel with a biomaterial to form a modified biocompatible hydrogel; and c) contacting the biological sample with the modified biocompatible hydrogel, wherein the hydrogel surrounds and encapsulates the sample. In certain non-limiting exemplary embodiments, the biomaterial is an anti-inflammatory peptide.

The cross-linked synthetic polymer hydrogels of the present invention are synthesized rapidly at physiological conditions without the production of toxic side products. Because the cross-linking is sufficiently rapid, the hydrogel can be formed in situ from a liquid precursor.

A. Biocompatible Macromonomers

The present invention provides new biocompatible macromonomers comprising a cyclic NHS ester group or a cysteine group. By "biocompatible" we mean a macromonomer that does not have toxic or injurious effects on biological systems and exhibits minimal local inflammatory response in surrounding tissues. For instance, the polyethylene glycol core (PEG) of one embodiment of the disclosed macromonomers is well-recognized as being biocompatible, as it is non-immunogenic and resistant to nonspecific protein and cell adhesions. The macromonomers of the present invention are useful in a wide variety of applications, including, for instance, tissue repair, wound healing, drug delivery, preventing surgical adhesions, as coatings on medical devices, and thin adherent hydrogels on biosensors and chip-based diagnostic devices for genomic and proteomic assays.

While PEG comprises the polymeric core in some embodiments, alternative polymeric cores including but not limited to linear or branched biocompatible polymers that can be similarly functionalized may also be used in the macromonomers of the present invention. By "functionalized" we mean modifying any linear or branched biocompatible polymer with N-terminal cysteine peptides as side chain functional groups or endgroups, or similar polymers functionalized with NHS esters. In a preferred embodiment, where PEG comprises the polymeric core of the macromonomer, there are eight arms emanating from the center of the macromonomer of the present invention. However, in alternative embodiments, the polymeric core could comprise two to eight or even ten to twenty different arms emanating from the center of the macromonomer.

B. Biocompatible Hydrogels

In some embodiments, the present invention provides new biocompatible hydrogels comprising covalently cross-linked NHS ester-polymer and N-terminal cysteine-polymer macromonomers. In previously disclosed NCL cross-linking using straight chain thioesters, hydrogel formation was inhibited under physiological conditions. Furthermore, cytotoxic free thiols were released to the surrounding medium. In contrast, in the present invention, hydrogel formation occurs in physiological conditions, and no toxic thiols are released to the surrounding medium.

By "biocompatible" we mean a hydrogel that does not have toxic or injurious effects on biological systems. The hydrogels of the present invention are useful in a wide variety of applications, including, for instance, medically useful devices or implants that can release bioactive compounds in a controlled manner for local, systemic, or targeted drug delivery; medically useful devices or implants for use as surgical adhesion prevention barriers, implantable wound dressings, scaffolds for cellular growth for tissue engineering or as surgical tissue adhesives or sealants; biomaterials for preventing transplant rejection; and other medically useful applications such as hydrogel coatings for preventing bacterial infection of medical device surfaces, and coatings for chip-based assays of DNA, RNA or proteins.

C. Methods of Synthesis

The invention also provides novel methods of synthesis of the biocompatible macromonomers and hydrogels described above. In general, the inventors first synthesized a first polymer macromonomer containing an HNS ester and a second polymer macromonomer containing an N-terminal cysteine residue. The macromonomers were then covalently cross-linked to form biocompatible hydrogels. The reaction conditions described herein lead to rapid hydrogel formation, and cell proliferation studies confirmed the non-toxic nature of the resulting hydrogels.

In one non-limiting exemplary embodiment, the methods comprise synthesizing and cross-linking an 8-armed PEG terminated with NHS (P8NHS) and an 8-armed PEG terminated with cysteine (P8Cys) through a mechanism similar to NCL to form a biocompatible hydrogel. The advantages of using NCL type methods as compared to other synthetic hydrogel formation techniques are that the reaction is very specific and the resulting product is biocompatible. The covalent cross-linking is initially limited to the cysteine and NHS ester groups on the PEG molecules, whereas in other hydrogel forming methods cross-linking can also occur between the synthetic macromonomers and biological components such as cell surface proteins and agents in the culture media. The hydrogel formation occurs under mild physiological conditions (pH 7-9), bearing a minimal toxicity to the cells during encapsulation. Further cross-linking occurs through the formation of disulfide bonds. Furthermore, the resultant hydrogel presents thiol groups that promote cell adhesion inside the hydrogel network and their mild reductive properties can also be used to protect encapsulated cells from oxidative stress.

The methods of macromonomer and hydrogel formation described herein provide biocompatible macromonomers and hydrogels which are easily modified with bioactive materials to improve functions of encapsulated cells such as supporting cell growth, and the development and secretion of cellular products upon biological stimulus. By "bioactive" we mean a substance that has or cause an effect on in biological samples. For example, the macromonomers and hydrogels may be further functionalized with peptides or other bioactive materials, such as proteins, growth factors, DNA, RNA.

D. Methods of Use

The biocompatible macromonomers and hydrogels of the present invention are useful in a wide variety of medically useful devices and implants. For instance, the biocompatible macromonomers of the present invention are useful in applications ranging from tissue repair, wound healing, drug delivery, preventing surgical adhesions, as coatings on medical devices, and thin adherent hydrogels on biosensors and chip-based diagnostic devices for genomic and proteomic assays.

The biocompatible hydrogels of the present invention are useful in forming medically useful devices or implants that can release bioactive compounds in a controlled manner for local, systemic, or targeted drug delivery. Further, the biocompatible hydrogels are useful in forming medically useful devices or implants for use as surgical adhesion prevention barriers, implantable wound dressings, scaffolds for cellular growth for tissue engineering or as surgical tissue adhesives or sealants. Further still, the biocompatible hydrogels are useful in forming peptide-functionalized hydrogels which can protect transplanted tissue from rejection. As a non-limiting example, such peptide-functionalized hydrogels could protect pancreatic islet cells from inflammatory response post-transplantation.

In one embodiment, the present invention provides a method of encapsulating a biological sample with biomaterials comprising preparing a biocompatible hydrogel according to the methods described above, reacting the biocompatible hydrogel with a biomaterial to form a modified biocompatible hydrogel, and contacting the biological sample with the modified biocompatible hydrogel, wherein the hydrogel surrounds and encapsulates the sample. By "biological sample" we mean to include a specimen or culture obtained from any source. Biological samples can be obtained from animals (including humans) and encompass fluids, solids, tissues, and gases. Biological samples include blood products, such as plasma, serum and the like. Such examples are not however to be construed as limiting the sample types applicable to the present invention.

By "biomaterials" we mean materials selected from the group consisting of anti-inflammatory agents, cell function promoting agents, various artificial implants, pacemakers, valves, catheters, and membranes (e.g., a dialyzer), as well as synthetic polymers such as polypropylene oxide (PPO) and polyethylene glycol (PEG). In a further preferred embodiment the biomaterial is an anti-inflammatory peptide such as an inhibitor of cell surface IL-1 receptor.

E. Kits

In another embodiment of the invention, a kit for preparing the biocompatible macromonomers and hydrogels of the present invention is provided. In one embodiment, the kit comprises a biocompatible macromonomer having an NHS ester group and a biocompatible macromonomer having a cysteine group, and instructions for use.

In a preferred embodiment, the kit comprises a powdered form of at least one of the biocompatible macromonomers, wherein the powdered macromonomer is hydrated by the user for immediate use, such as in a dual syringe device to form a precursor liquid that rapidly gels. Optionally, the kit may contain a solution for dissolving the macromonomer.

In another preferred embodiment, the kit comprises at least one of the biocompatible hydrogels discussed above and instructions for use.

In an alternate embodiment, the kit comprises a biocompatible hydrogel according to the present invention formulated, delivered and stored for use in physiologic conditions.

By "instructions for use" we mean a publication, a recording, a diagram, or any other medium of expression which is used to communicate the usefulness of the invention for one of the purposes set forth herein. The instructional material of the kit can, for example, be affixed to a container which contains the present invention or be shipped together with a container which contains the invention. Alternatively, the instructional material can be shipped separately from the container or provided on an electronically accessible form on a internet website with the intention that the instructional material and the biocompatible hydrogel be used cooperatively by the recipient.

EXAMPLES

The following examples are, of course, offered for illustrative purposes only, and are not intended to limit the scope of the present invention in any way. Indeed, various modifications of the invention in addition to those shown and described herein will become apparent to those skilled in the art from the foregoing description and the following examples and fall within the scope of the appended claims.

Example 1

Materials

PEG-OH (8 Arm, MW 20082) and PEG-NH$_2$ (8 Arm, MW 19715) were purchased from JenKem Technology USA Inc. (Allen, Tex., USA).

Glutaric anhydride, N,N-diisopropylethylamine (DIEA), 1,2-ethanedithiol (EDT), triisopropylsilane (TIS), L-cysteine (L-Cys), S-methyl-L-Cysteine, N-acetyl-L-Cysteine, glutaric acid, dibasic sodium phosphate (Na$_2$HPO$_4$), potassium chloride (KCl), sodium chloride (NaCl), N-hydroxysuccinimide (NHS) and ethidium homodimer-1 were purchased from Sigma (St. Louis, Mo., USA).

The coupling reagent 1-Ethyl-3-(3-dimethylaminopropyl) carbodiimide hydrochloride (EDC) was purchased from TCI America (Portland, Oreg., USA).

Boc-Cys(Trt)-OH and Calcein AM were purchased from Santa Cruz Biotechnology, Inc. (Santa Cruz, Calif., USA).

Benzotriazole-1-yl-oxy-tris-pyrrolidino-phosphonium hexafluorophosphate (BOP) was purchased from Advanced ChemTech (Louisville, Ky., USA).

Porcine pericardium was purchased from Animal Technologies, Inc. (Tyler, Tex., USA).

The 3T3-swiss albino fibroblasts were purchased from the American Type Culture Collection center (Manassas, Va., USA).

Trifluoroacetic acid (TFA) and β-mercaptoethanol were purchased from Merk KGaE (Darmstadt, Germany).

Hematoxylin and eosin were purchased from Leica Microsystems (Buffalo Grove, Ill., USA).

Picro-sirius red was purchased from Poly Scientific (Bay Shore, N.Y., USA).

Monobasic potassium phosphate (KH$_2$PO$_4$) and permount mounting medium were purchased from Fisher Scientific (Waltham, Mass., USA).

Dulbecco's phosphate buffered saline (PBS) (pH 7.0) without calcium or magnesium (Life Technologies, Grand Island, N.Y., USA) was used to prepare hydrogels and included 2.67 mM KCl, 137.93 mM NaCl, 1.47 mM KH$_2$PO$_4$ and 8.06 mM Na$_2$HPO$_4$ (PBS). Hydrogels prepared with this buffer and used in vitro were incubated in excess PBS (pH 7.0) or culture medium following gelation (not more than 15 minutes of gelation).

NMR, pH measurements, and part of the gelation kinetics experiments were done with phosphate buffer (100 mM PBS) which was prepared from PBS substituted with additional KH$_2$PO$_4$ and Na$_2$HPO$_4$ and included 2.67 mM KCl, 137.93 mM NaCl, 15 mM KH$_2$PO$_4$ and 85 mM Na$_2$HPO$_4$. Other concentrations of PBS were prepared by diluting 100 mM PBS with saline (2.67 mM KCl, 137.93 mM NaCl).

Example 2

Synthesis of Glutaric Acid-Terminated 8 Arm PEG (P8G)

Figure 21:
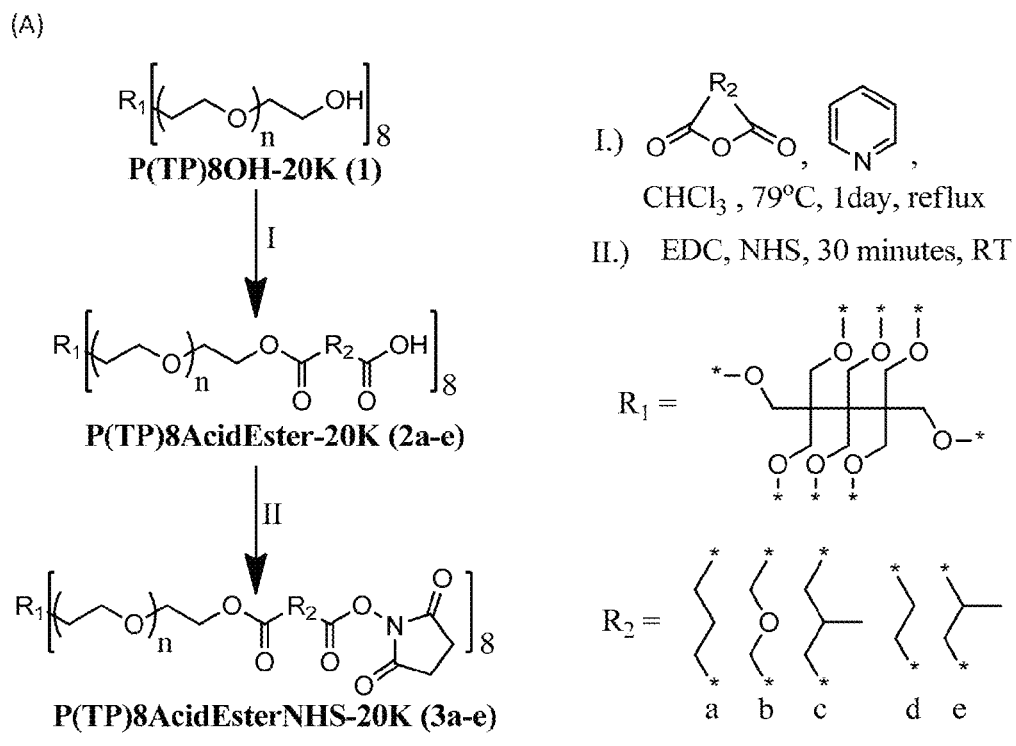
FIG. 21. (A) Synthesis of NHS-terminated PEG derivatives. In step I, the terminal hydroxyl group of PEG is reacted with an anhydride to form a terminal carboxyl group with variable PEG to carboxyl spacers (i.e., $R_2$). In step II, the terminal carboxyl groups are activated with an NHS ester. Products 2a-e correspond to examples 2-5 respectively. Products 3a-e correspond to examples 6-10 respectively. (B) Chemical structure of the products described in examples 6-10.
Figure 21:
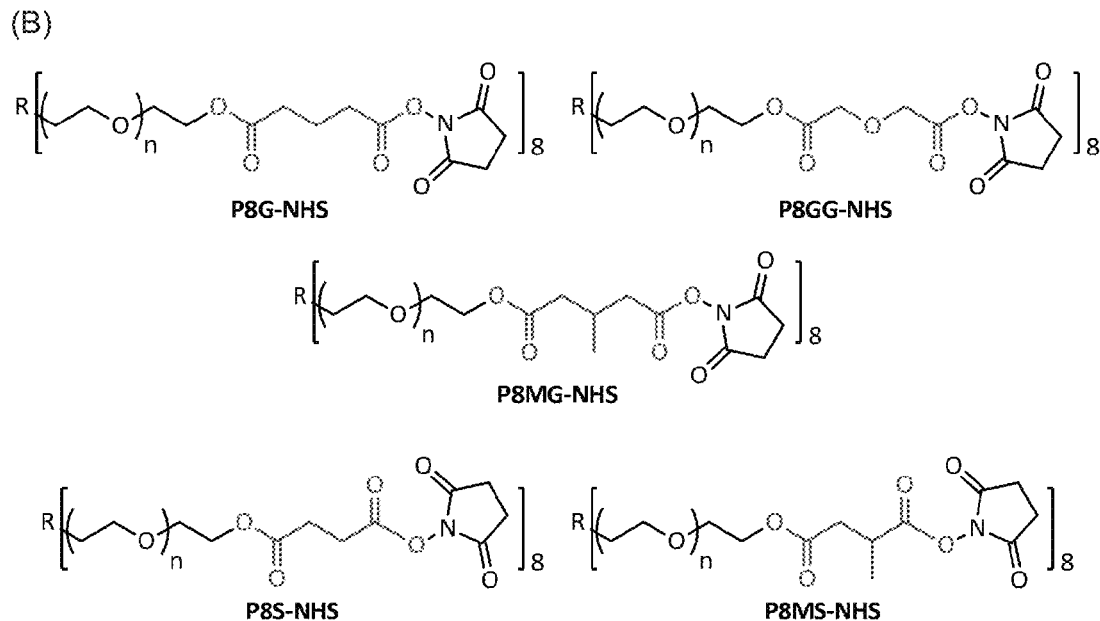

Glutaric acid-terminated PEG (P8G) was synthesized by dissolving 8-arm PEG-OH (20 g, 7.97 mmol OH or 1 equivalent OH) and glutaric anhydride (4.54 g, 39.84 mmol, or 5 equivalents) in chloroform (2.5 mL chloroform per 1 mmol OH). Pyridine (5 eq) was added dropwise, and the reaction mixture was refluxed at 80° C. for 24 hours under inert air. The product was diluted with MeOH (240 mL or 12 mL MeOH per gram of PEG), precipitated at −20° C. for 1 hour, and centrifuged at −5° C. The supernatant was discarded, and the MeOH wash procedure was repeated twice more. Following diethyl ether precipitations (180 mL or 9 mL ether per gram of PEG), the product was dried under high vacuum overnight to afford a white powder (97.6% yield, 100% conversion). See FIG. 21.

1H NMR (500 MHz, CDCl$_3$), δ, ppm: δ 4.24 (2H, t, terminal PEG CH$_2$), δ 3.64 (1823H, m, backbone PEG CH$_2$), δ 2.43 (2H, t, C2 of glutaric acid), δ 2.39 (2H, t, C4 of glutaric acid), δ 1.95 (2H, p, C3 of glutaric acid).

Example 3

Synthesis of Glycol Glutaric Acid-Terminated 8 Arm PEG (P8GG)

The same procedure used to synthesize P8G was used to synthesize P8GG, with the exception that diglycolic anhydride was used instead of glutaric anhydride (91% yield, 99.9% conversion).

Example 4

Synthesis of 3-Methyl Glutaric Acid-Terminated 8 Arm PEG (P8MG)

The same procedure used to synthesize P8G was used to synthesize P8MG, with the exception that 3-methyl glutaric anhydride was used instead of glutaric anhydride (87.1% yield, 102.9% conversion).

Example 5

Synthesis of Methyl Succinic Acid-Terminated 8 Arm PEG (P8MS)

The same procedure used to synthesize P8G was used to synthesize P8MS, with the exception that methyl succinic anhydride was used instead of glutaric anhydride (79.5% yield, 99.3% conversion).

Example 6

Synthesis of N-Hydroxysuccinimide (NHS)-Terminated 8 Arm PEG (P8G-NHS)

NHS-terminated 8 arm PEG (P8G-NHS) was synthesized by dissolving P8G (20 g, 7.62 mmoL or 1 equivalent COOH), NHS (8.77 g, 76.20 mmol or 10 equivalents) and EDC (14.61 g, 76.20 mmol or 10 equivalents) in DMSO (50 mL or 2.5 mL DMSO per gram of PEG). After 30 minutes of stirring at room temperature, the product was diluted with MeOH (500 mL or 25 mL MeOH per gram of PEG), precipitated at −20° C. for 1 hour, and spun down at −5° C. The supernatant was discarded, and the MeOH wash procedure was repeated twice more. Following diethyl ether precipitations (480 mL or 25 mL ether per gram of PEG), the product was dried under high vacuum overnight to afford a white powder (80.6% yield, 97.4% conversion). See FIG. 21B.

1H NMR (500 MHz, CDCl$_3$), δ, ppm: δ 4.24 (2H, t, terminal PEG CH$_2$), δ 3.64 (1961H, m, backbone PEG CH$_2$), δ 2.84 (4H, m, NHS protons), δ 2.71 (2H, t, C4 of glutaric acid), δ 2.49 (2H, t, C2 of glutaric acid), δ 2.06 (2H, p, C3 of glutaric acid).

Example 7

Synthesis of N-Hydroxysuccinimide (NHS)-Terminated 8 Arm P8GG (P8GG-NHS)

The same procedure used to synthesize P8G-NHS was used to synthesize P8GG-NHS, with the exception that P8GG was used instead of P8G (85.1% yield, 68.9% conversion).

Example 8

Synthesis of N-Hydroxysuccinimide (NHS)-Terminated 8 Arm P8MG (P8MG-NHS)

The same procedure used to synthesize P8G-NHS was used to synthesize P8MG-NHS, with the exception that P8MG was used instead of P8G (92.2% yield, 95% conversion).

Example 9

Synthesis of N-Hydroxysuccinimide (NHS)—Terminated 8 Arm P85 (P85-NHS)

The same procedure used to synthesize P8G-NHS was used to synthesize P8S-NHS, with the exception that P8S was used instead of P8G (93.6% yield, 97.1% conversion).

Example 10

Synthesis of N-Hydroxysuccinimide(NHS)—Terminated 8 Arm P8MS (P8MS—NHS)

The same procedure used to synthesize P8G-NHS was used to synthesize P8MS-NHS, with the exception that P8GG was used instead of P8MS (81.8% yield, 98.5% conversion).

Example 11

Synthesis of Cysteine Terminated 8 Arm PEG (P8Cys)

Cysteine-terminated 8 arm PEG (P8Cys) was synthesized using BOP as a coupling reagent. In one reaction vessel, 8 arm PEG amine (13.4 g, 5.44 mmol NH$_2$) was dissolved in DMF (25 mL) and DIEA was added dropwise (947 μL, 5.44 mmol). In a separate reaction vessel, Boc-Cys(Trt)-OH (10.0 g, 21.75 mmol) and BOP (9.62 g, 21.75 mmol) were dissolved in DMF (25 mL) and DIEA (3.79 mL, 21.75 mmol) was added dropwise. Five minutes after adding DIEA, the BOP solution was combined with the PEG solution and the coupling reaction was allowed to proceed at room temperature for 18 hours. Following precipitation in cold diethyl ether (2800 mL), the product was re-dissolved in MeOH (70 mL) and precipitated in cold diethyl ether once more (280 mL). The cysteine was deprotected with TFA:TIS:EDT (210 mL, 95:2.5:2.5) cleavage solution at room temperature for 4 hours. TFA was evaporated under low pressure, and the product was precipitated in cold diethyl ether (160 mL). P8Cys was dissolved in MeOH (120 mL), precipitated at −20° C. for 1 hour, and centrifuged at −5° C. The supernatant was decanted and the MeOH precipitation was repeated twice more. Following diethyl ether precipitations (30 mL), the product was dried under high vacuum overnight to afford an extra pure white powder (50% yield, 86% conversion).

1H NMR (500 MHz, Acetic Acid-d$_4$), δ, ppm: δ 4.42 (1H, t, 6-C cysteine), δ 3.69 (1872H, m, backbone PEG CH$_2$), δ 3.13 (2H, d, CH$_2$ cysteine).

Example 12

Hydrogel Preparation Using P8G-NHS

PBS was used to prepare 10% (w/v) P8G-NHS and 10% (w/v) P8Cys and the two solutions were mixed in a 1:1 (v/v) ratio to form cylindrical 704 hydrogels (5 mm diameter×3.5 mm height).

Example 13

Hydrogel Preparation Using P8GG-NHS

PBS was used to prepare 10% (w/v) P8GG-NHS and 10% (w/v) P8Cys and the two solutions were mixed in a 1:1 (v/v) ratio to form cylindrical 704 hydrogels (5 mm diameter×3.5 mm height).

Example 14

Hydrogel Preparation Using P8MG-NHS

PBS was used to prepare 10% (w/v) P8MG-NHS and 10% (w/v) P8Cys and the two solutions were mixed in a 1:1 (v/v) ratio to form cylindrical 70λ hydrogels (5 mm diameter×3.5 mm height).

Example 15

Hydrogel Preparation Using P8S-NHS

PBS was used to prepare 10% (w/v) P8S-NHS and 10% (w/v) P8Cys and the two solutions were mixed in a 1:1 (v/v) ratio to form cylindrical 70λ hydrogels (5 mm diameter×3.5 mm height).

Example 16

Hydrogel Preparation Using P8MS-NHS

PBS was used to prepare 10% (w/v) P8MS-NHS and 10% (w/v) P8Cys and the two solutions were mixed in a 1:1 (v/v) ratio to form cylindrical 70λ hydrogels (5 mm diameter×3.5 mm height).

Example 17

NMR Analysis of Reaction Between L-Cys and P8NHS

All reactions were done at room temperature. First, 100 mM PBS (pH adjusted to either 6.0 or 7.0) was lyophilized, redissolved in the same volume of $D_2O$, and then used to prepare solutions of L-cysteine (57 mM) and P8NHS (10 w/v %, 38 mM NHS ester). The two solutions were mixed in a 1:1 v/v ratio and reaction kinetics followed using $^1H$ NMR in a Varian Inova 500 MHz NMR. Similar experiments were carried out in pure $D_2O$ as described above by mixing solutions of L-Cys (29 mM) and P8NHS (1.25% w/v, 5 mM NHS ester).

Figure 2:
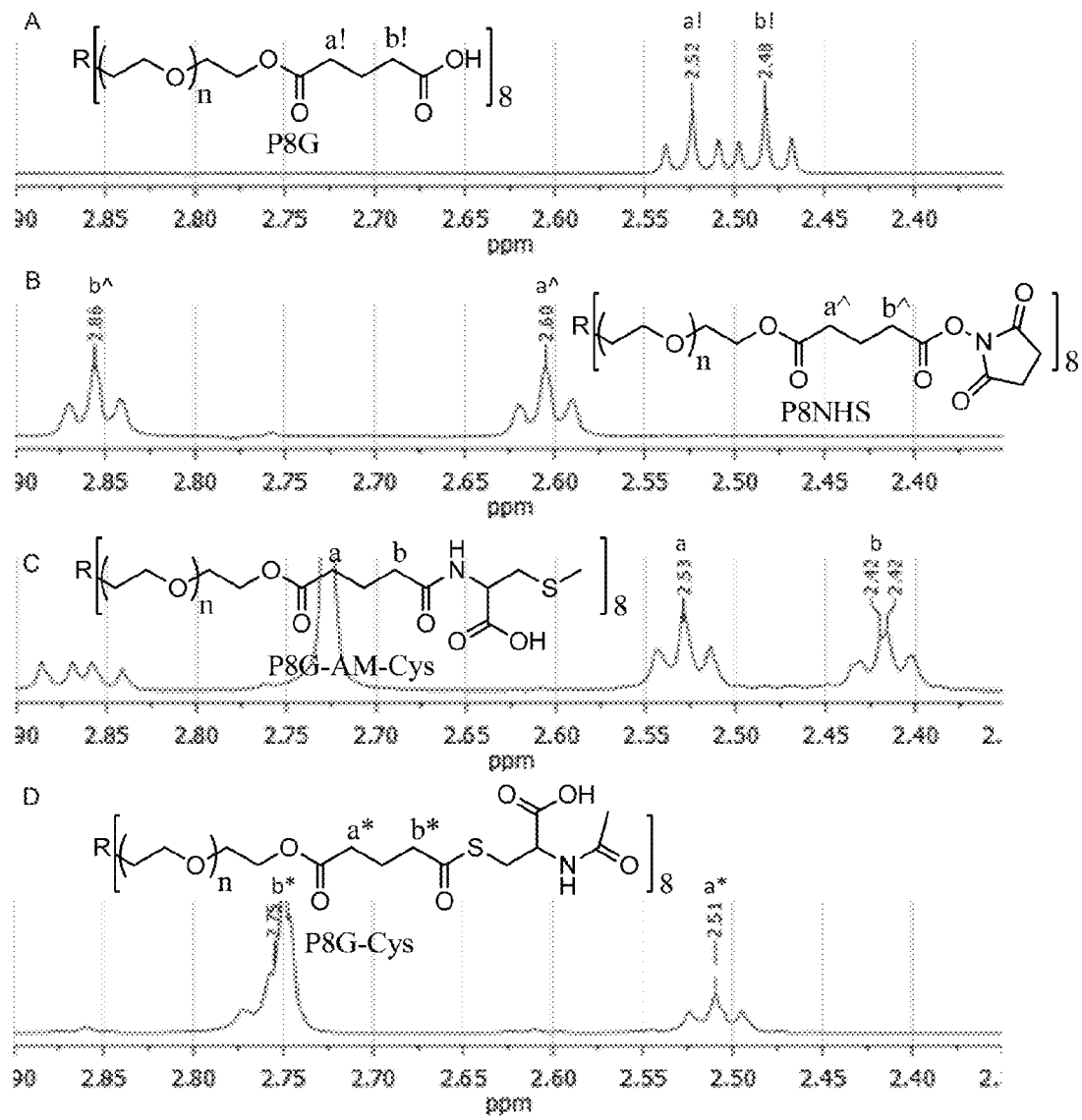
FIG. 2. 1H NMR spectra and peak assignments for (A) P8G, (B) P8NHS, (C) P8G-TE-N-acetyl-Cys, and (D) P8G-AM-S-methyl-Cys in $D_2O$. The chemical shifts of the C2 and C4 protons of P8G-TE-N-acetyl-Cys and P8G-AM-S-methyl-Cys were taken as representative of P8G-TE-Cys and P8G-AM-Cys, respectively, in the calculation of relative abundance (RA) of species.

The relative abundance (RA) of polymer species during the OMNCL reaction between P8NHS and L-Cys was determined by integrating the triplets associated with the protons bound to the C2 and C4 carbons of the terminal glutarate linker. In this reaction four polymer species are possible (P8NHS, PBG, P8G-TE-Cys, P8G-AM-Cys), each possessing slightly different chemical shifts of the C2 and C4 protons depending on the composition of the terminal group (FIG. 2 and Table 1).

TABLE 1

$^1H$ NMR chemical shift peak assignments used in calculation of relative abundance of species during reaction of P8NHS with L-Cys.

PEG-O-C(=O)-C2-C4-C(=O)-R

| Species | C2 | C4 |
|---|---|---|
| P8NHS | 2.61 | 2.86 |
| P8G | 2.52 | 2.47 |
| P8G-TE-Cys | 2.52 | 2.81 |
| P8G-AM-Cys | 2.52 | 2.43 |

The chemical shifts for the protons associated with the C2 and C4 carbons of glutarate of P8G and P8NHS were determined from spectra of the synthesized intermediate and final product (see above), whereas the chemical shifts of thioester (P8G-TE-Cys) and amide (P8G-AM-Cys) linked products were estimated from spectra obtained by reaction of P8NHS with N-acetyl-L-cysteine and S-methyl-L-cysteine, respectively. Integrated peak values were used in the equations below to calculate the relative abundance of each species present during the reaction of P8NHS and L-Cys.

$$RA_{P8G} = \frac{\delta_{2.47}}{\delta_{2.61} + \delta_{2.52}} \quad (1)$$

$$RA_{P8NHS} = \frac{\delta_{2.61}}{\delta_{2.61} + \delta_{2.52}} \quad (2)$$

$$RA_{P8G-TE-Cys} = \frac{\delta_{2.52} - \delta_{2.47} - \delta_{2.43}}{\delta_{2.61} + \delta_{2.52}} \quad (3)$$

$$RA_{P8G-AM-Cys} = \frac{\delta_{2.43}}{\delta_{2.61} + \delta_{2.52}} \quad (4)$$

Example 18 pH Measurement

PBS (100 mM PBS and dilutions of the buffer) was used to prepare 38 mM L-cysteine and 10% (w/v) P8NHS (38 mM NHS ester). The two solutions were mixed in a 1:1 v/v ratio and the pH of the reaction mixture was followed over time using a standard pH meter (Accumet Titration Controller, Model 150, Fisher Scientific, Waltham, Mass., USA) and electrode (Beckman 511275-AB Electrode, Beckman, Pasadena, Calif., USA).

Example 19

Gelation Time

The time to form a hydrogel was measured using a previously described protocol.[22] Briefly, 10% (w/v) P8NHS and 10% (w/v) P8Cys were prepared in phosphate buffered saline (PBS, 100 mM PBS, or dilutions of 100 mM PBS). The two solutions were then mixed in a 1:1 (v/v) ratio and pipetted up and down using a standard 2-200 μL pipette tip. The time at which the material blocked the pipette tip was designated as the gelation time. Temperature was controlled within the range 4-60° C. through the use of a water bath.

Example 20

Hydrogel Swelling

PBS was used to prepare 10% (w/v) P8NHS and 10% (w/v) P8Cys and the two solutions were mixed in a 1:1 (v/v) ratio to form cylindrical 70 μL hydrogels (5 mm diameter×3.5 mm height). The gels were allowed to set for 15 minutes and then transferred to PBS. The wet weights of the gels were measured at various time points, and buffer was replaced at least 5 times a week. At 5 hours, half of the hydrogels (n=5) were exposed to reducing agent (0.2 M β-mercaptoethanol in PBS) and swelling was monitored until equilibrium was reached for both groups. At 303 hours the hydrogels equilibrated in PBS were exposed to reducing agent and swelling was monitored until 447 hours, after which the hydrogels were transferred back to PBS and swelling was followed until equilibrium was reached. The hydrogel swelling experiments were all carried out under room temperature and with five replicates per group. Relative wet weight was calculated as defined in equation 5, where $w_0$ is the initial wet weight and $w_t$ is the wet weight of the hydrogel at time t.

$$\text{Relative Wet Weight} = \frac{w_t}{w_0} \quad (5)$$

Example 21

Mechanical Testing

The compressive moduli and adhesive strength of the hydrogel (10% w/v, 1:1 w/w P8NHS:P8Cys, prepared in PBS) were measured at room temperature with a Syntech Model #20G screw actuation testing machine equipped with 250 g and 1000 lb load cells. Compressive moduli were measured using cylindrical hydrogels (6.5 mm height×8.5 mm diameter) that were swollen for 5, 75 or 150 hours in PBS. The hydrogels were compressed along their axes between two flat plates, and the equilibrium stress was recorded for strains between 1 and 10%. The Young's modulus was calculated by measuring the slope of the linear portion of the stress vs. strain curve.

The adhesive strength of the hydrogel was measured using a lap shear test adapted from ASTM standard F2255-05. Unprocessed porcine pericardium (2.5 cm×3 cm) was adhered to aluminum fixtures using a cyanoacrylate based adhesive and then covered with a PBS moistened paper. After 1 hour, 100 µL of hydrogel precursor was placed on one tissue surface and a second tissue surface brought into contact (2.5 cm×1.25 cm overlap) such that the tissue sections were glued together. After 10 minutes of curing, the tissue and glue were covered with PBS moistened paper towel for an additional 50 minutes. The glued tissue was pulled apart at 5 mm/min in tensile shear, and the peak stress and tissue overlap area were used to calculate the adhesive strength of the material.

Example 22

Cytotoxicity

Cytotoxicity was evaluated using two methods. For the first assay, the guidelines found in ISO standards 10993-05 and 10993-12 were used. Briefly, 3T3 fibroblasts were exposed to polymer precursor or hydrogel extract. Extracts were prepared by suspending a 200 µL hydrogel in 1 mL of culture medium (n=3); alternatively, P8NHS was dissolved directly in culture medium to yield a 5% (w/v) solution (n=3). These solutions were then incubated at 37° C., 5% $CO_2$ and >90% RH for 24 hours, diluted to various concentrations using fresh medium, and 100 µL of each dilution added to a subconfluent monolayer of 3T3 fibroblasts in 96 well plates (n=3). The cells were incubated in the presence of the conditioned medium at 37° C., 5% $CO_2$ and >90% RH for 24 hours. After washing with PBS the cells were exposed for 3 hours to 0.4% neutral red prepared in DMEM. The cells were again washed with PBS and destained using 1% glacial acetic acid, 50% ethanol and 49% $ddH_2O$. Following 10 minutes of agitation, absorbance at 540 nm was used to quantify viability. Culture medium and 0.2% SDS were used as a negative and positive control and were incubated along with the extracts at 37° C., 5% $CO_2$ and >90% RH for 24 hours prior to addition to the subconfluent monolayer of cells. Per the requirements stated in the ISO standard, $IC_{50}$ of the positive control SDS was found to be within the acceptable range, confirming the validity of the assay.

In the second viability assay, cells were suspended in the P8Cys component dissolved in PBS and mixed with the P8NHS component dissolved in PBS to yield a 7% (w/v) hydrogel containing 1:1 (w/w) ratio of P8Cys to P8NHS. The hydrogels were allowed to set for 1 to 2 minutes and then incubated in culture medium at 37° C. and 5% $CO_2$. After 24 hours, cell viability was quantified using calcein AM and ethidium homodimer-1. Cells were stained for 15 minutes in culture medium substituted with 4 µM calcein AM and 4 µM ethidium homodimer-1. Images were acquired using a fluorescent microscope equipped with a 485±10 nm optical filter for calcein AM (live cells) and a 530±12.5 nm optical filter for ethidium homodimer-1 (dead cells). The images were merged and processed using ImageJ (National Institute of Health, Bethesda, Md.).

Example 23

In Vivo Studies

B10.BR male mice were obtained from the Jackson Laboratories (Bar Harbor, Me., USA). The mice were housed in the Animal Facility of the Wistar Institute and all treatments were approved by the Wistar IACUC. At 10 weeks of age, mice were injected subcutaneously at the base of the neck with 100 µL of 10% (w/v) 1:1 (w/w) ratio of P8Cys to P8NHS hydrogel prepared in PBS. Six weeks later, mice were euthanized and tissue together with the hydrogel were removed and fixed in 4% buffered formalin for 24 hours. Tissue was then washed, dehydrated through serial ethanol washes, cleared with xylene and embedded in paraffin overnight. Tissue sections of 5-10 µm thickness were cut and mounted on superfrost slides (VWR, Radnor, Pa., USA).

Tissue sections were cleared, rehydrated, and then stained with hematoxylin and eosin or with picro-sirius red, dehydrated, cleared with xylene and coverslipped with Permount mounting media. Staining was visualized using an Olympus (AX70) microscope (Olympus America, Center Valley, Pa., USA) in bright field for H&E and under polarized light for Picro-Sirius Red. Images were recorded using a Spot camera with bounded software.

Example 24

Statistical Analysis

One-way ANOVA was used to detect significant effects among groups. Tukey's multiple comparison tests were used to detect significant differences between groups, and a p-value ≤0.05 was considered significant.

Results.

Polymer Synthesis and Hydrogel Formation.

Figure 3:
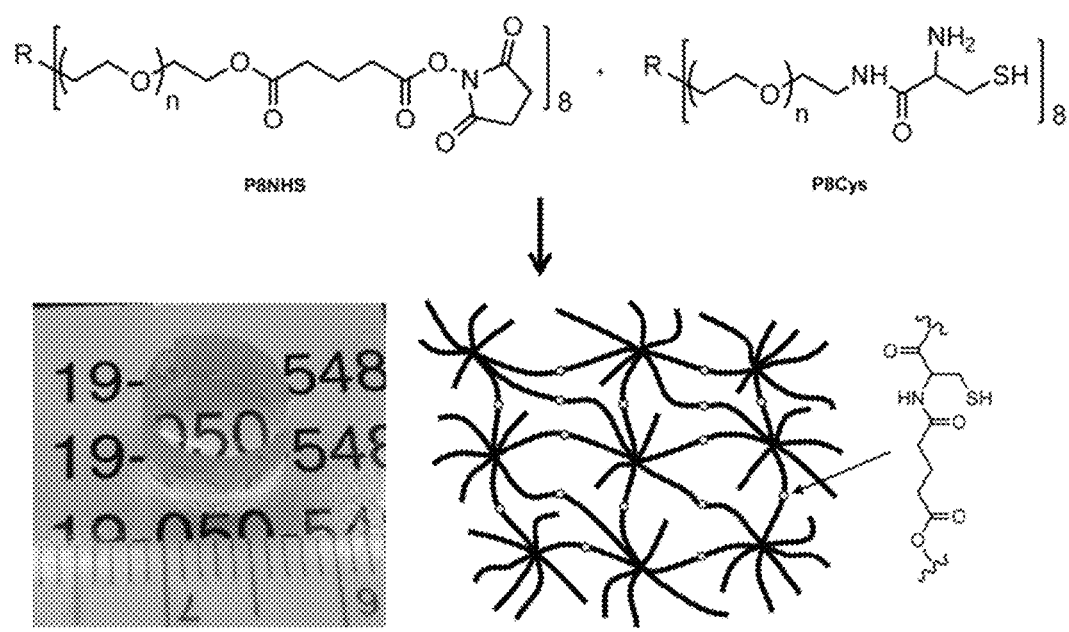
FIG. 3. The two polymer precursors P8NHS and P8Cys react in aqueous solution via OMNCL to yield polymer hydrogels with network cross-links as shown at bottom right.

P8NHS was synthesized with an overall yield of approximately 95% through a two-step reaction involving addition of a glutaric acid linker to an 8-arm PEG followed by activation of terminal acid groups with NHS. P8Cys was synthesized in one step from amine terminated 8-arm PEG and N,S-protected Cys amino acid followed by deprotection and purification for a yield of 50%. Within approximately 20 seconds of mixing P8Cys and P8HNS the solution became noticeably viscous and solidified to form a stiff hydrogel (FIG. 3). Under the same conditions, a hydrogel formed within approximately 240 seconds when P8Cys was replaced with the 8-arm PEG-NH$_2$ polymer used to synthesize P8Cys, suggesting the reaction mechanism between P8Cys and P8NHS involves thiol capture followed by a S-to-N acyl rearrangement (OMNCL) rather than a direct reaction between the activated ester of P8NHS and the terminal amine of P8Cys.

Mechanism of Hydrogel Formation.

Figure 4:
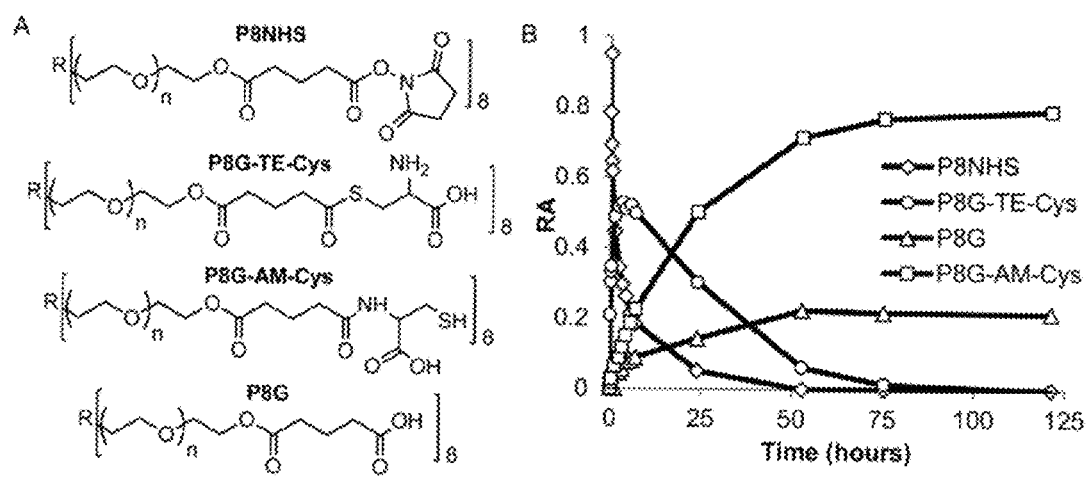
FIG. 4. Quantitative $^1H$ NMR analysis of the model reaction between P8NHS and L-Cys in $D_2O$. Chemical structures (A) and relative abundance (B) of polymer species observed during the reaction.
Figure 5:
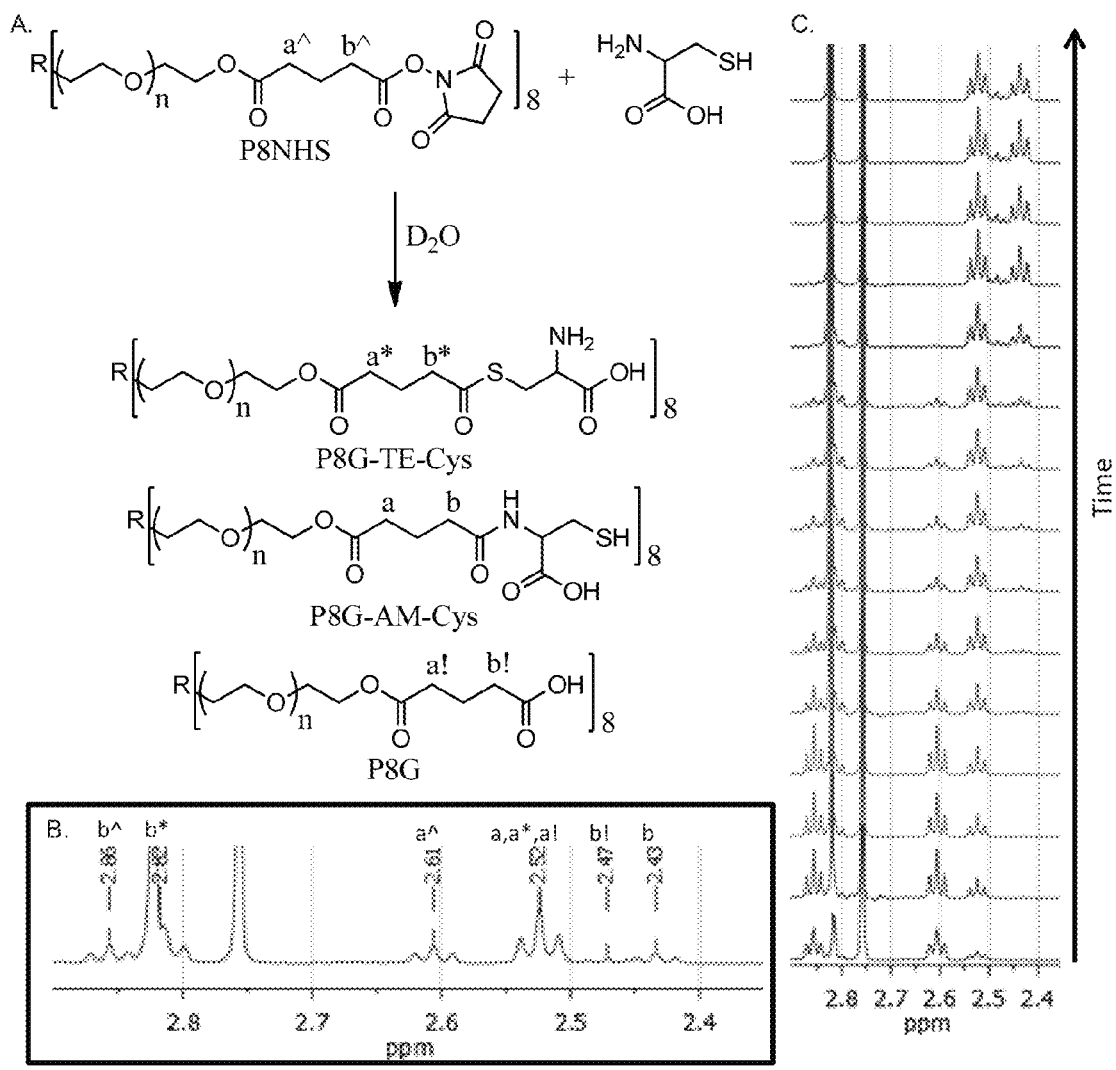
FIG. 5. Kinetics of the reaction between P8NHS (1.25% (w/v), 5 mM NHS ester) and L-cysteine (29 mM) in unbuffered $D_2O$. The two solutions were mixed in a 1:1 v/v ratio and the reaction followed by $^1H$ NMR. (A) The four polymer species P8NHS, P8G-AM-Cys, P8G-TE-Cys and P8G were observed throughout the progress of the reaction. The protons on carbons C2 and C4 were used to quantify their relative abundances according to Equations 1-4. (B) The proton chemical shifts were 2.52 ppm for a!, 2.47 ppm for b!, 2.86 ppm for b^, 2.61 ppm for a^, 2.52 ppm for a*, 2.82 ppm for b*, 2.52 ppm for a and 2.43 ppm for b. (C) The spectra shown correspond to reaction times ranging from 4.3 minutes to 121 hours. The disappearance of P8NHS peaks occurs as P8G-TE-Cys and P8G-AM-Cys peaks emerge.

In model experiments designed to elucidate the reaction mechanism, the buffered and unbuffered reaction between P8NHS and L-Cys were analyzed by $^1$H NMR. We determined the relative abundance of four major polymer species with time during the reaction: the NHS activated polymer precursor (P8NHS), hydrolysis product (P8G), the thioester formed by thiol capture of L-Cys by P8NHS (P8G-TE-Cys), and the amide linked product (P8G-AM-Cys) (FIG. 4A). Analysis of the $^1$H NMR spectra acquired for up to 120 h after mixing revealed clear chemical shift changes corresponding to the appearance and disappearance of the reactants, intermediates and products (FIG. 5). Spectral analysis using peak assignments obtained from reference spectra (FIG. 2) and calculation of relative abundance according to equations 1-4 revealed the temporal progression of the reaction (FIG. 4B).

Figure 6:
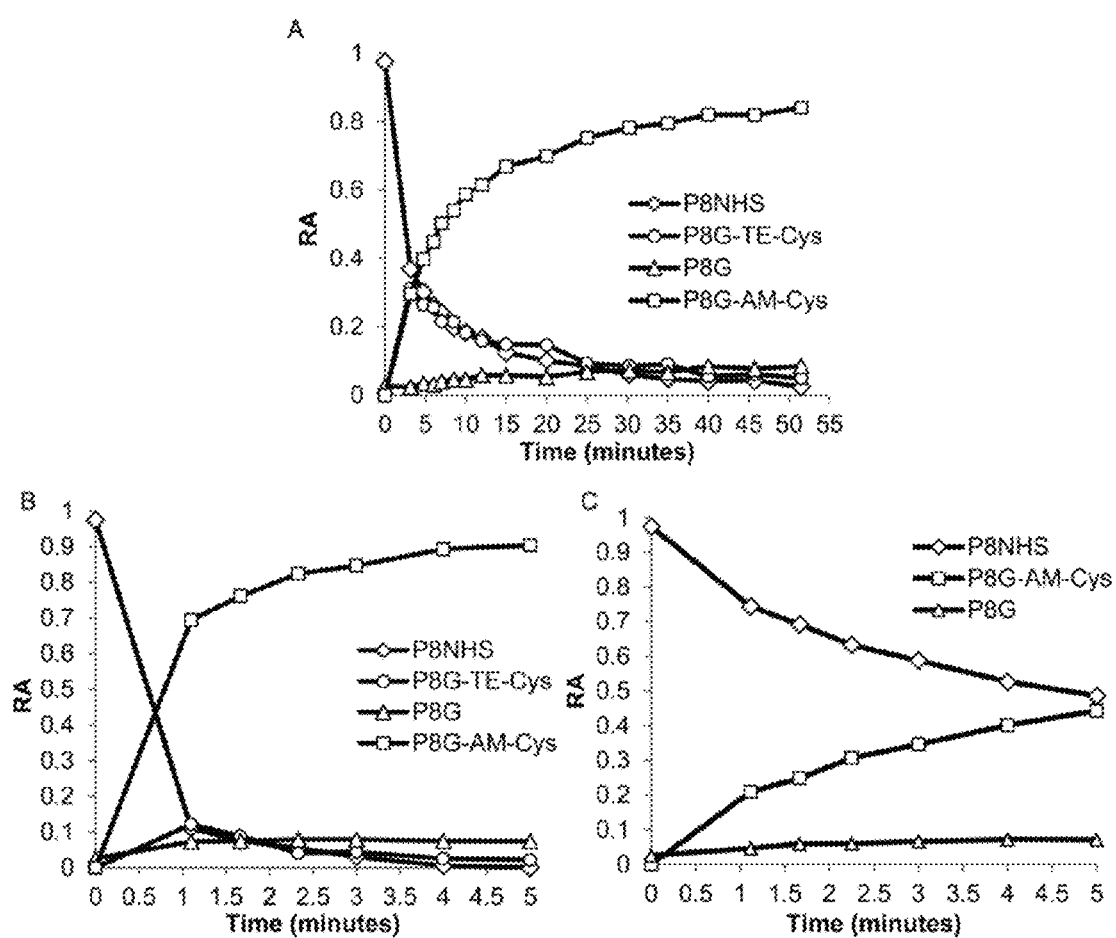
FIG. 6. Quantitative $^1H$ NMR analysis of the reaction between P8NHS and L-Cys in buffered $D_2O$. (A,B) Relative abundance of polymer species formed during reaction of P8NHS with L-Cys at (A) pH 6.0 and (B) pH 7.0, indicating that the reaction proceeds more quickly at higher pH. (C) Relative abundance of polymer species formed during the reaction of P8NHS with S-methyl-L-cysteine at pH 7.0, illustrating significantly slower reaction kinetics when the thiol group is protected.
Figure 7:
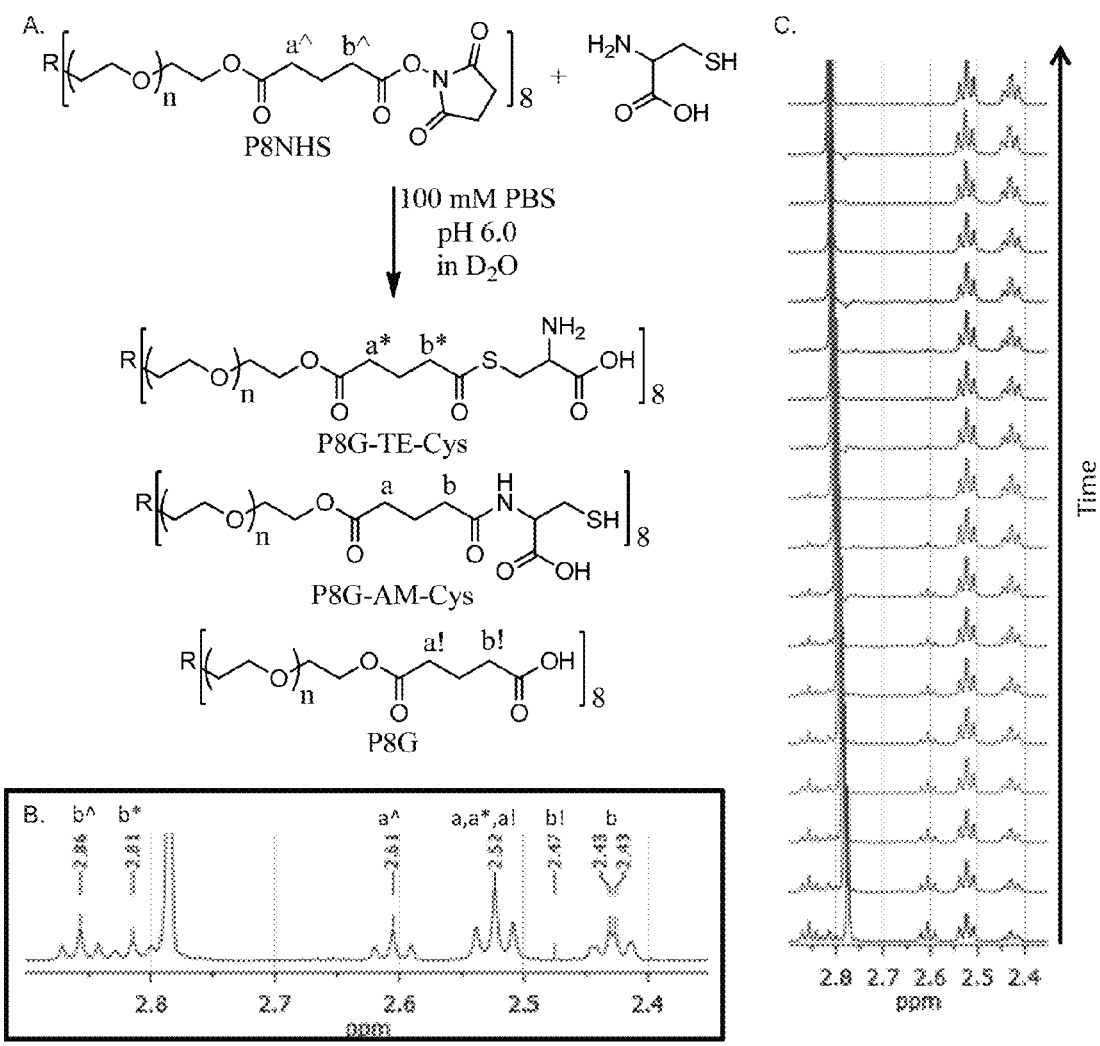
FIG. 7. Kinetics of the reaction between P8NHS (10% (w/v), 38 mM NHS ester) and L-cysteine (57 mM) in buffered $D_2O$, pH 6.0. The two solutions were mixed in a 1:1 v/v ratio and the reaction followed by $^1H$ NMR. (A) The four polymer species P8NHS, P8G-AM-Cys, P8G-TE-Cys and P8G were observed throughout the progress of the reaction. The protons on carbons C2 and C4 were used to quantify their relative abundances according to Equations 1-4. (B) The proton chemical shifts were 2.52 ppm for a!, 2.47 ppm for b!, 2.86 ppm for b^, 2.61 ppm for ^, 2.52 ppm for a*, 2.81 ppm for b*, 2.52 ppm for a and 2.43 ppm for b. (C) The spectra shown correspond to reaction times ranging from 3.2 to 85 minutes. The disappearance of P8NHS peaks occurs as P8G-TE-Cys and P8G-AM-Cys peaks emerge.

Upon mixing P8NHS and L-Cys, rapid disappearance of P8NHS was accompanied by rapid emergence of the thioester intermediate P8G-TE-Cys. P8G-TE-Cys reached a maximum value after several minutes and slowly started to disappear thereafter and was found in only trace amounts after 75 h (FIG. 4B). Concomitant with disappearance of P8G-TE-Cys, the amide linked product P8G-AM-Cys emerged slowly over the first hour and represented over approximately 80% of species present in the reaction mixture after 75 h. P8G appeared in minor but detectable amounts, present at less than about 20% at all time points. Similar trends were observed when the reaction of P8NHS and L-Cys was performed in the presence of phosphate buffer at pH 6, albeit with significantly faster kinetics (FIG. 6A and FIG. 7). At pH 7, the reaction was essentially complete within 5 minutes (FIG. 6B).

Figure 8:
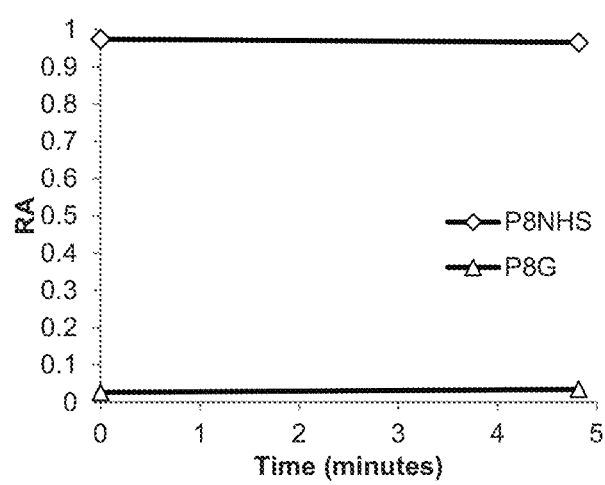
FIG. 8. Kinetics of NHS hydrolysis for P8NHS in pH 7.0 buffer. Lyophilized 100 mM PBS (pH 7.0) was re-dissolved in $D_2O$ and used as the solvent for NMR analysis at a concentration of 10% (w/v) P8NHS (38 mM NHS ester). The relative abundance of P8G remained below 0.1 during the first 5 minutes of the reaction.
Figure 9:
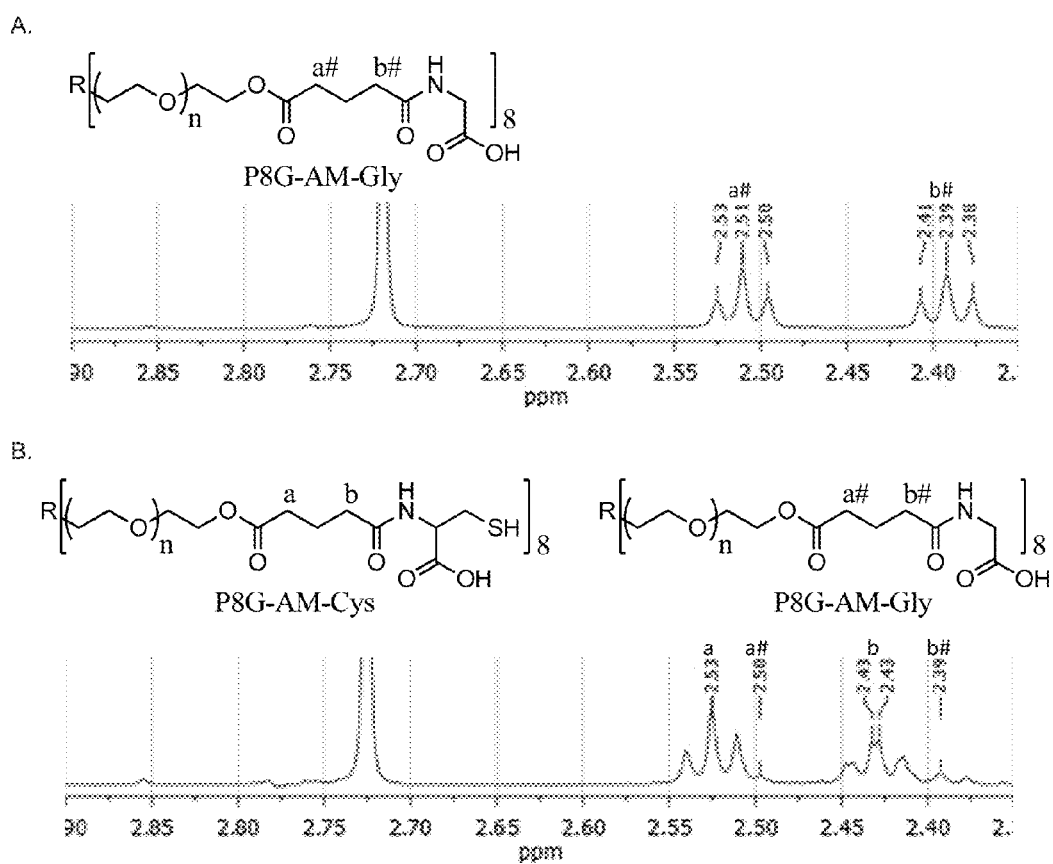
FIG. 9. Reaction of P8NHS with L-Cys and L-Gly. (A) Peak assignment for C2 and C4 protons of P8G-AM-Gly in $D_2O$. (B) Reaction between P8NHS (10% (w/v), 38 mM NHS ester) and L-cysteine (57 mM) plus L-Gly (57 mM) in buffered $D_2O$, pH 7.0. The two solutions were mixed in a 1:1 v/v ratio and the ¹H NMR spectrum of the reaction mixture after 8 minutes is shown. Spectral analysis indicated that 80% of the product was P8G-AM-Cys, 15% was P8G-AM-Gly and 5% was P8G.
Figure 10:
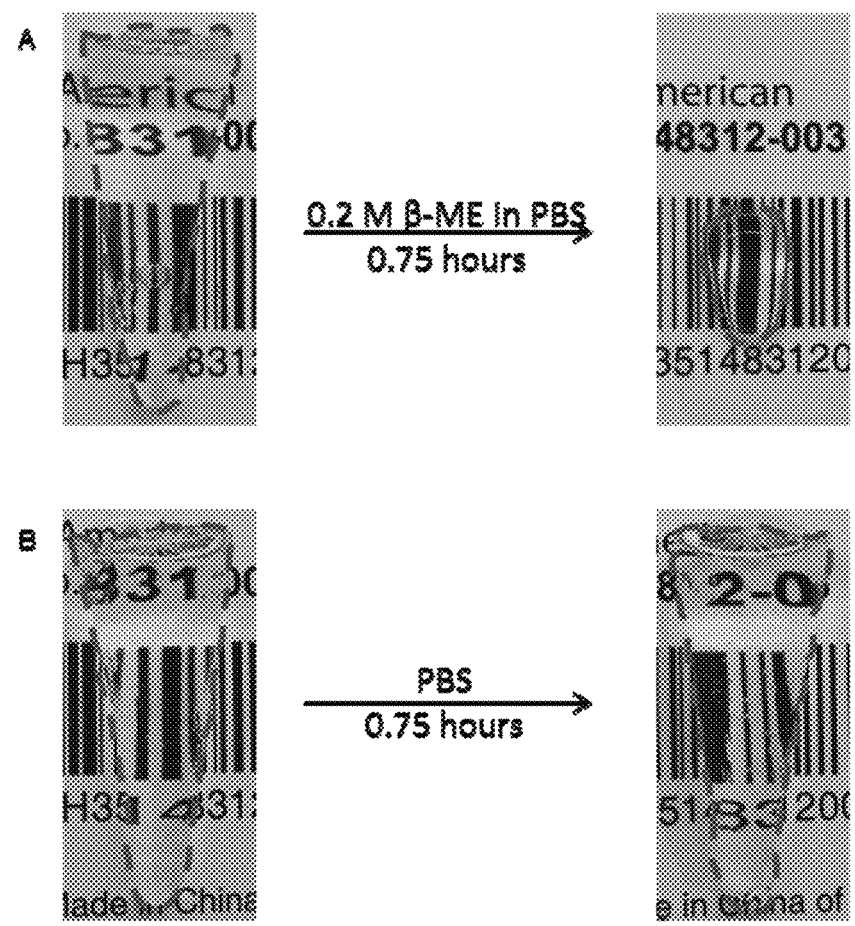
FIG. 10. P8NHS plus L-Cys form hydrogels. In a microcentrifuge tube, 19 mM L-Cys in 100 mM PBS (pH 7.0) was mixed in a 1:1 v/v ratio with 10% (w/v) P8NHS (38 mM NHS ester) in 100 mM PBS (pH 7.0), forming stable hydrogels within 2 hours. (A) Incubation of one such hydrogel for 0.75 hours in PBS containing 0.2 M β-mercaptoethanol resulted in partial solubilization of the gel, and after 1.25 hours the gel was completely solubilized. (B) Following incubation of another such hydrogel for 0.75 hours in pure PBS demonstrated that the hydrogel remained intact. The edges of the hydrogels are marked with dashed lines.

Under the same conditions, control experiments showed that hydrolysis of P8NHS was insignificant within this timeframe (FIG. 8). At pH 7, when L-Cys was replaced with S-methyl-L-cysteine, the reaction was significantly slower (FIG. 6C) despite the lower pKa of the amino group of S-methyl-L-cysteine (8.75[23] vs. 10.78 for L-Cys[23]). In a separate experiment at pH 7, P8NHS was reacted with equal concentrations of both L-Cys and L-Gly (amine pKa 9.6[23]), yielding 80% P8G-AM-Cys, 15% P8G-AM-Gly and 5% P8G (FIG. 9). Interestingly, mixtures of 10% (w/v) P8NHS (38 mM NHS ester) and 19 mM L-Cys were observed to form stable gels after 2 hours of incubation (100 mM PBS, pH 7.0), although these gels liquefied in the presence of β-mercaptoethanol but not PBS (FIG. 10), implying cross-linking via disulfide bond formation.

The crosslinking mechanism between P8Cys and P8NHS leads to the formation of two distinct crosslink types (Table 2). One type of crosslink is a result of the thiol attacking the NHS ester to form a thioester. The proximity and orientation of the primary amine in relation to the thioester leads to a rearrangement to form a more stable and hence more permanent amide bond. This mechanism of amide bond formation via a rearrangement is similar to native chemical ligation (NCL), with the exception that a more reactive NHS ester is used as opposed to a thioester.[14]

TABLE 2

Crosslinking mechanism between P8Cys and P8NHS:

| | Thiol Attacks NHS Ester | NHS Release | First Crosslink (Thioester) | Rearrangement (Amide) | Second Crosslink (Disulfide Bridge) | |
|---|---|---|---|---|---|---|
| Polymer Interaction | | | | | | |
| Chemical Structure Of Crosslink | | | | | | |

Figure 23:
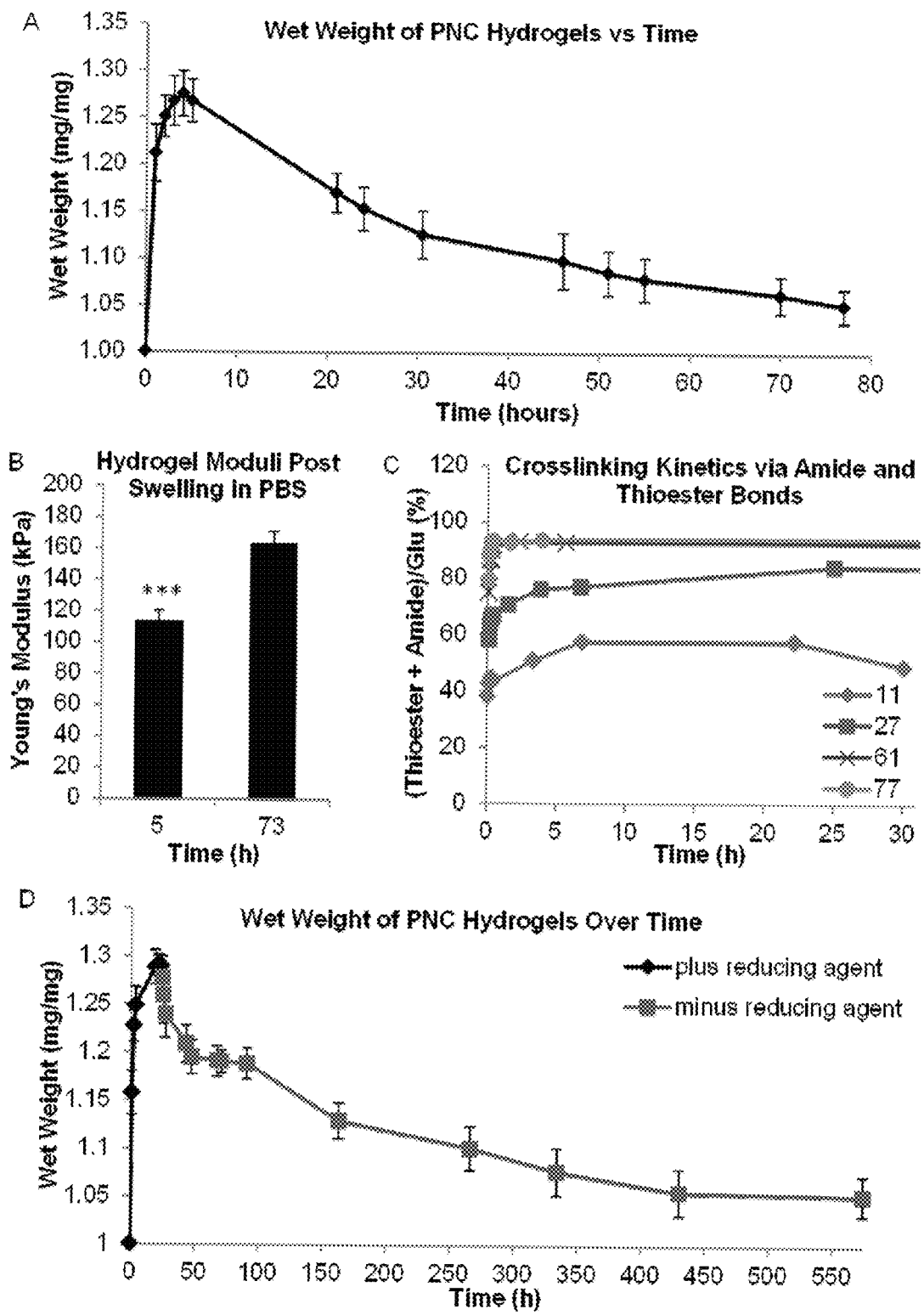
FIG. 23. Supporting data for disulfide bond formation. (A) Swelling in PBS and (B) young's moduli for 10% (w/v) 1:1 (P8Cys:P8NHS) hydrogels prepared with 11 mM phosphate buffer in saline. (C) Thioester+amide bonds per glutaric acid over time for various concentrations of phosphate buffer (mM). (D) Wet weight of hydrogels at swelling equilibrium that were expoosed to a reducing agent for 23 hours (diamond) and then the reducing agent was removed (square).

The second crosslink, a disulfide bond, leads to a decrease in swelling and improved mechanical properties. Since hydrogels are hydrophilic materials, once they set they may imbibe physiological fluid which can lead to a significantly increase in volume. For example, PEG based hydrogels crosslinked via amide or thioester bonds alone can swell up to 50%[15] and 400%[16] within the first 24 hours. In some cases, swelling of implanted materials may lead to complications such as nerve compression[17-21] or other serious problems requiring reoperation.[22] The consequent symptoms may range from uncomfortable to life threatening. The tissue adhesive material presented herein is crosslinked both via amide and disulfide bonds. The rearrangement step introduces free thiols that subsequently react with each other to form disulfide bridges further crosslinking the material (FIG. 23). As a result of the extra crosslinking, the hydrogels exhibit minimal swelling. Since the PNC hydrogel shows minimal equilibrium swelling (5%, FIG. 23A) and maintains a high adhesive strength, it may be ideal for applications where an increase in hydrogel volume can lead to complications.

Physical Characterization of Hydrogels.

Figure 11:
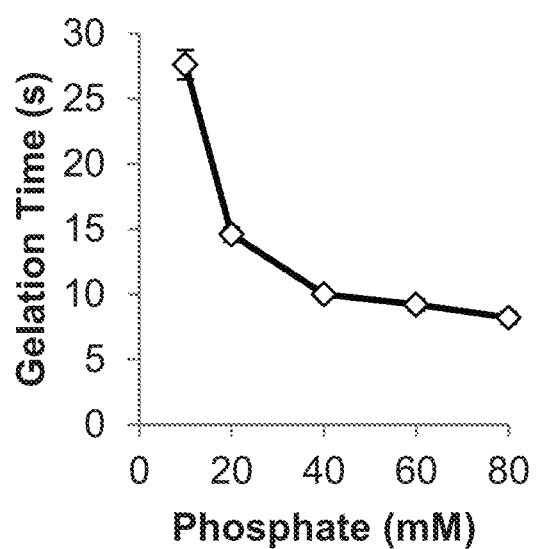
FIG. 11. The effect of phosphate buffer concentration on gelation kinetics of 10% w/v hydrogels prepared in PBS (dilutions of 100 mM PBS) at room temperature with P8Cys and P8NHS (1:1 w/w). The plot shows gelation time versus phosphate buffer concentration for an initial buffer pH of 7.3.
Figure 12:
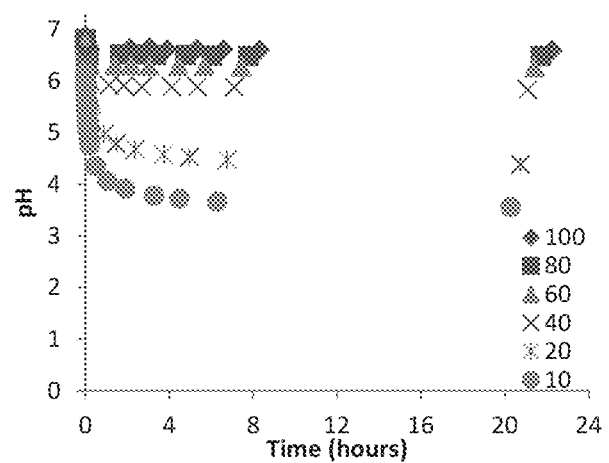
FIG. 12. Change in pH during the reaction of P8NHS with L-Cys as a function of phosphate buffer concentration (10 to 80 mM, initial pH 7.3).

Buffer concentration, pH and temperature were found to strongly influence the rate of gel formation. As the phosphate buffer concentration (initial pH 7.3) was increased from 10 to 80 mM, gel time decreased from about 28 s to less than 9 s, respectively (FIG. 11). As we could not measure the pH within the hydrogel itself, instead we measured the pH of a P8NHS/L-Cys reaction mixture under equivalent conditions in order to ascertain pH changes during the reaction. As shown in FIG. 12, the pH was found to decrease with time during the reaction. Reaction solutions with higher buffer concentration yielded smaller pH changes, with buffer concentrations of 80 mM exhibiting a pH drop of 0.8 pH units during the reaction. Hence, higher buffer concentration led to faster gelation and a lower drop in pH, implying that the reaction is accelerated at high pH.

Figure 13:
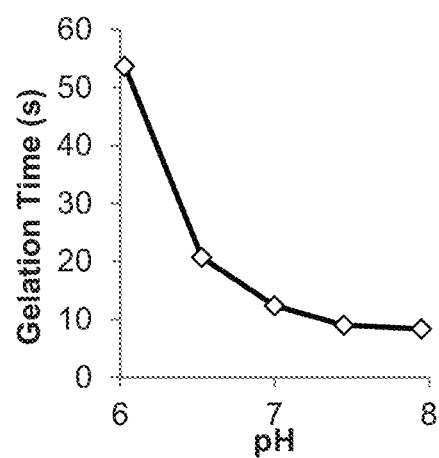
FIG. 13. The effect of initial pH on gelation time of 10% w/v hydrogels prepared in 100 mM PBS at room temperature with P8Cys and P8NHS (1:1 w/w).
Figure 14:
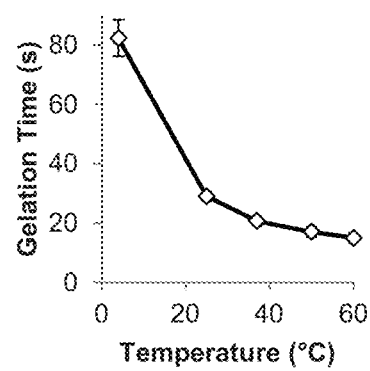
FIG. 14. The effect of temperature on gelation time of 10% w/v hydrogels prepared with P8Cys and P8NHS (1:1 w/w) in 10 mM phosphate buffered saline (initial pH 7.0).

These findings led us to select a buffer concentration of 100 mM for gel kinetic studies under different pH conditions. The pH dependence of gelation time for a 10% w/v mixture of P8NHS and P8Cys in 100 mM PBS is shown in FIG. 13. It can be seen in this figure that gel time changed significantly within the pH range 6-8, ranging from about 50 s at pH 6 to <10 s at pH 8. Finally, we determined the temperature dependence of gelation time, which showed that gel formation was accelerated by about 9 s when the temperature was changed from room to body temperature (FIG. 14).

Figure 15:
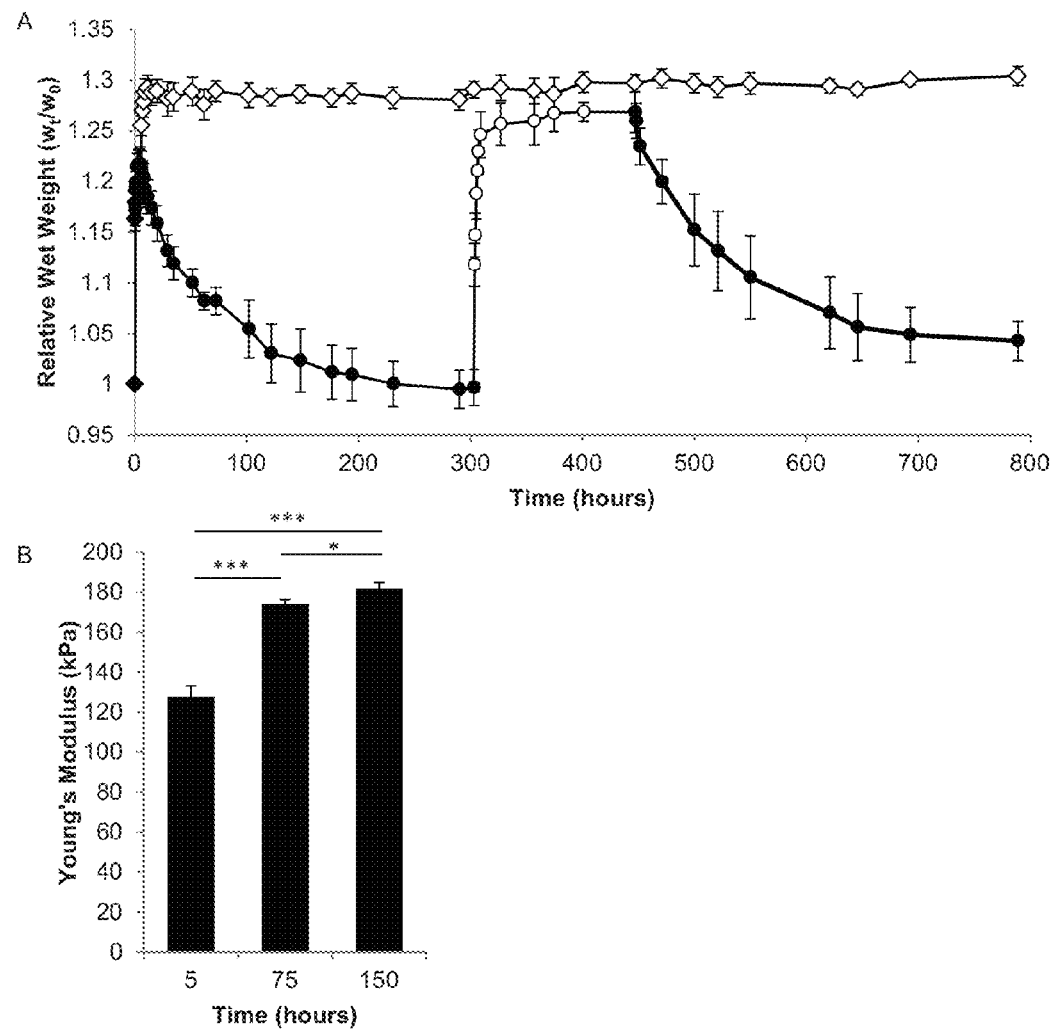
FIG. 15. Physical characterization of OMNCL hydrogels formed by mixing equal volumes of 10% (w/v) P8NHS and 10% (w/v) P8Cys in PBS. (A) Swelling of OMNCL hydrogels in 10 mM PBS (closed symbols) or 10 mM PBS substituted with 0.2 M β-ME (open symbols). The two sets of hydrogels (diamonds and circles, n=5 per set) varied by the sequence in which they were incubated in PBS or β-ME. In one case (circles), the hydrogels were incubated in PBS followed by β-ME and then PBS again. In the second case (diamonds), the hydrogels were incubated in PBS for the first few hours and thereafter in β-ME. (B) Young's moduli (n=4) at various time points for OMNCL hydrogels incubated in PBS. * p<0.05, *** p<0.001.
Figure 16:
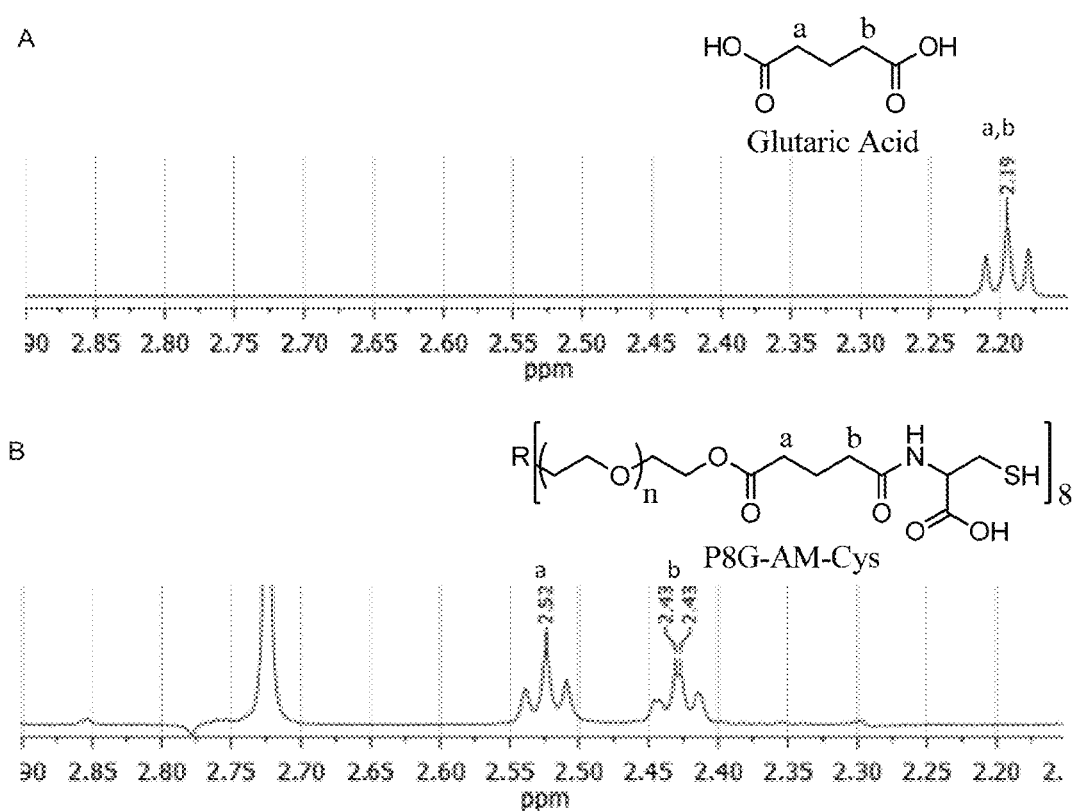
FIG. 16. Analysis of potential hydrolysis for the ester between glutaric acid and PEG. Lyophilized 100 mM PBS (pH 7.0) was re-dissolved in $D_2O$ and used as the solvent for NMR analysis. (A) The 1H NMR spectrum of pure glutaric acid (5 mg/mL) showed that the protons located on carbons 2 and 4 of glutaric acid appear at 2.19 ppm. (B) ¹H NMR spectrum for the reaction mixture of P8NHS and L-Cys at pH 7.0 at about 5 minutes, revealing no appreciable hydrolysis of the ester between glutaric acid and PEG.
Figure 17:
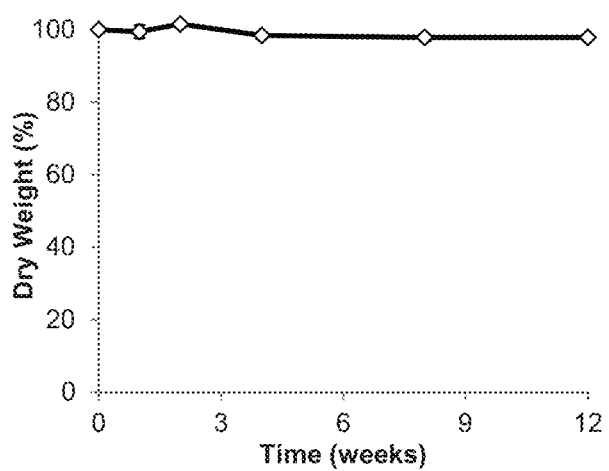
FIG. 17. OMNCL hydrogel degradation in PBS. P8Cys and P8NHS were dissolved in PBS to yield 10% (w/v) solutions, mixed in a 1:1 (v/v) ratio, and allowed to gel for 15 minutes before being transferred into 2 mL of PBS. The 70 μL hydrogels were incubated at 37° C., and at various time points, 3 hydrogels were each washed with $ddH_2O$ before lyophilizing and dry weights measured. Following 12 weeks of incubation, no significant loss of dry weight was observed.

Several types of mechanical characterizations were undertaken on hydrogels formed from P8NHS with P8Cys. Swelling experiments were performed by immersing hydrogel samples in excess PBS and measuring the weight changes as a function of time. OMNCL hydrogels increased in relative wet weight by approximately 21% in the first several hours and then slowly contracted over a period of many hours to a final increase in relative wet weight of approximately 0% (FIG. 15A). The young's modulus of the hydrogel was measured at 5, 75 and 150 h and was found to increase from 128 to 182 kPa during this time (FIG. 15B). The latent modulus increase is unlikely to be attributed to additional cross-linking by the OMNCL mechanism, as model 1H NMR studies showed that at pH 7 the reaction was mostly complete after 5 minutes (FIG. 6B). The observed swelling and modulus changes are unlikely to reflect mass changes induced by hydrolytic degradation of the gels, as NMR analysis of ester hydrolysis (FIG. 16) and a preliminary evaluation of gel degradation at pH 7.0 showed little mass loss over a 12 week period (FIG. 17).

Suspecting therefore that gel shrinkage was the result of disulfide bond formation, fully equilibrated hydrogels (>300 hours swelling in PBS) were transferred into 0.2 M β-mercaptoethanol in PBS, whereupon the hydrogels increased in relative wet weight by approximately 27% (FIG. 15A). After approximately 140 hours in reducing agent, swollen samples were transferred back into PBS and swelling was observed to decrease once again, implying the re-formation of disulfide bonds.

Finally, the adhesive strength of the OMNCL hydrogel to unprocessed porcine pericardium was measured in lap shear similar to the protocol described in ASTM standard F2255-05. Tissue surfaces were glued together using the OMNCL hydrogel and then pulled apart after one hour post gelation, yielding a lap shear adhesive strength of 46±8 kPa.

Cytotoxicity. The cytotoxicity of the hydrogel was tested using two methods. The first method was conducted in accordance with ISO standards 10993-5 and 12, from which it was concluded that the OMNCL hydrogel as well as P8HNS polymer (5% w/v solution) were not toxic to cells as viability remained well above 90% (FIG. 18A). It was not possible to analyze P8Cys precursor in this cytotoxicity assay, as a 5% (w/v) solution of P8Cys in cell culture medium solidified within 3 hours, presumably via disulfide bond formation. In the second test, cells were encapsulated in OMNCL hydrogels and viability was quantified after 24 hours using calcein AM and ethidium homodimer-1. In this assay we observed that 87±7% of the encapsulated cells remained viable 1 day following encapsulation (FIG. 18B).

In Vivo Studies.

Subcutaneous injections of OMNCL hydrogel were administered to B10.BR male mice, and after 6 weeks the implants were extracted and processed for histological analysis. The results showed the remnants of an acute inflammatory response typical of PEG based hydrogels. H&E stained histological sections showed that the surrounding tissue was intact. A low number of inflammatory cells were observed in the vicinity of the implant, and a thin fibrous capsule formed around the hydrogel (FIG. 19A, B), as indicated by positive staining for collagen fibrils with Picro-Sirius red under polarized light illumination (FIG. 19C).

Discussion.

Figure 22:
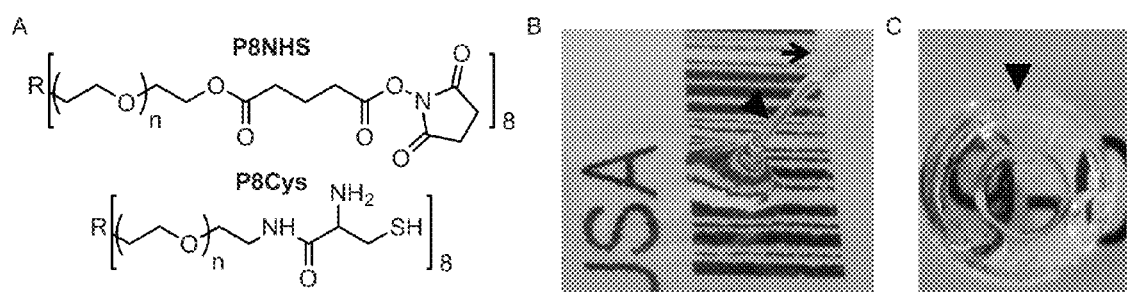
FIG. 22. (A) The two components P8NHS and P8Cys are first dissolved in aqueous buffer. (B) When the two are mixed together, the solution turns viscous within seconds and forms a stiff hydrogel (arrowhead) that clogs the pipette tip (arrow). (C) Top view of a self-standing cylindrical hydrogel (arrowhead). The hydrogel was prepared using the cap of an Eppendorf tube as a mold.

We have detailed the synthesis, reaction mechanism and characterization of a two-component hydrogel formulation that sets rapidly by OMNCL at physiologic pH and ionic strength. The material is clear (FIG. 22) which makes it an attractive candidate for wound closure in ophthalmic surgery or other such areas of medicine where light obstruction is undesirable. The OMNCL reaction involves covalent capture of the thiol side chain of N-terminal Cys to initially form a thioester bond. The proximity and orientation of the primary amine in relation to the thioester leads to a S-to-N acyl rearrangement to form the more stable amide bond. This mechanism of amide bond formation via rearrangement is similar to native chemical ligation (NCL),[24] with the exception that in OMNCL a oxo-ester is employed as opposed to a thioester (FIG. 1).[18]

Implementation of NCL in a biological context can be problematic due to the adverse biological effects of the buffers and reducing agents typically employed in NCL reactions. Furthermore, we have shown that the small molecule thiol leaving group liberated during NCL can be toxic to cells.[13] OMNCL, on the other hand, is often practiced in solutions containing concentrated guanidine (5-6M),[18-20] which would have adverse effects in a biological system because of its strong denaturing potential. Our results show that hydrogel formation by OMNCL proceeds well in phosphate buffer, achieving rapid gel formation without the use of catalysts or additives. In the pH range of our experiments (pH 6-7.3), the rate of gel formation by OMNCL was adjustable through pH control and ranged from several seconds to less than a minute. This is in contrast to gels formed by NCL chemistry,[7,12] which have slower gelation rates at physiological pH.

We elucidated the mechanism of cross-linking by following the reaction of P8NHS and L-Cys by 1H NMR (FIGS. 4 and 6A, B), taking advantage of chemical shift differences to reveal the temporal evolution of reactants, intermediates and products. Several lines of evidence from these studies point to cross-link formation via OMNCL. First, the rapid increase in thioester cross-link in parallel with the rapid decrease in P8NHS at the beginning of the reaction is indicative of thiol capture. The thioester intermediate reaches as high as >50% relative abundance within the first few minutes but then decreases until it is no longer detectable. This decrease cannot be explained by thioester hydrolysis, as the hydrolysis product (P8G) was never present at greater than about 10% relative abundance at pH 6 or 7. Second, the kinetics of thioester cross-link disappearance was roughly matched with the kinetics of amide cross-link emergence, which is a strong indicator of S-to-N rearrangement. It should be noted that at neutral and acidic pH the thiol should be considerably more reactive than the primary amino group due to the high pKa of the terminal amine of L-Cys (pKa about 10.78[23]). As evidence of this, in the reaction between P8NHS and L-Cys at neutral pH, conversion to P8G-AM-Cys and P8G-TE-Cys was 83% within the first minute. However, reaction of P8NHS with S-methyl-L-Cys yielded only 20% conversion under the same conditions, despite the significantly lower pKa of the S-methyl-L-Cys amino group (pKa about 8.75)[23] compared to L-Cys. Finally, further support for OMNCL pathway was provided by a competitive reaction between P8NHS, L-Cys and L-Gly, where 80% of the reaction proceeded with L-Cys and only 15% with L-Gly despite the lower amino pKa of L-Gly (pKa about 9.6[23]).

Figure 20:
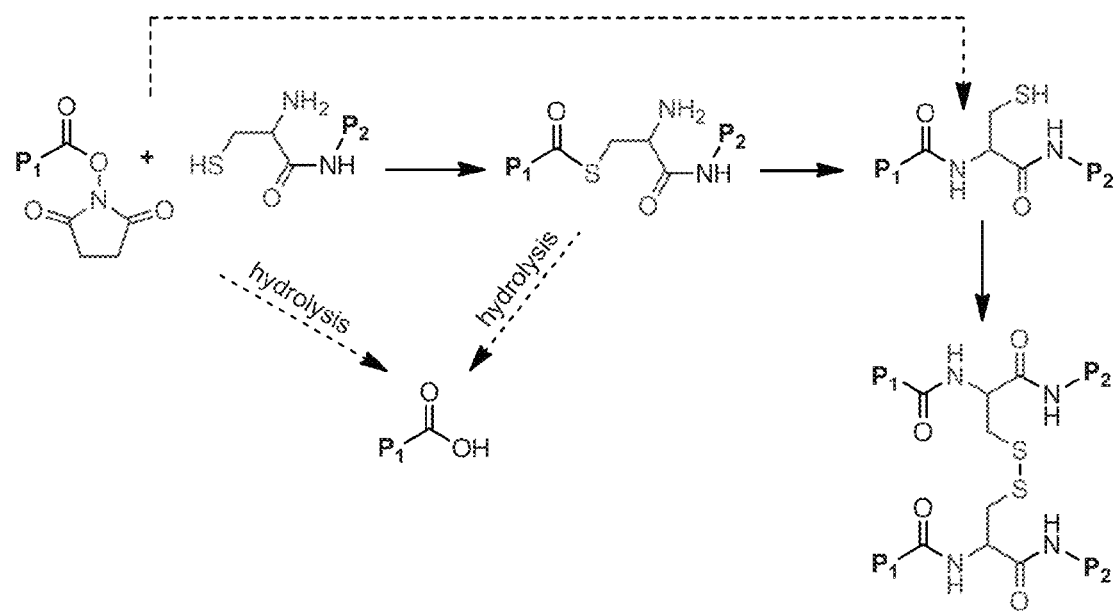
FIG. 20. OMNCL crosslinking of P8Cys and P8NHS. Fast reaction pathways are indicated by solid arrows, slow pathways by dashed arrows. Thiol capture followed by S-to-N acyl rearrangement results in polymer cross-linking. Secondary cross-links arise through the formation of disulfide bonds among network-bound Cys residues. $P_1$=P8NHS; $P_2$=P8Cys.

Taking these findings into consideration, we therefore propose the OMNCL reaction pathway shown in FIG. 20 for the gel-forming reaction between P8NHS and P8Cys. For reasons elaborated above, we consider the hydrolysis of P8NHS and the thioester intermediate as minor competing reactions under our conditions. Both of these reactions would produce acid terminated polymer endgroups that would not be capable of contributing to gel formation. It is impossible to exclude some contribution from direct amide bond formation between the terminal amine of P8Cys and P8NHS. However, it should be noted that the pKa value of the N-terminal amino of Cys is 10.78 whereas that of the thiol side chain is 8.33.[23] Thus, at the pH values of 6-7.3 employed in gel formation, most N-terminal amino groups of Cys would be rendered inactive toward reaction with the NHS activated ester by protonation. In support of this, mixtures of P8NHS and 8-arm PEG-amine form gels more than 10 times slower in PBS buffer.

Most polymer hydrogels typically absorb water under physiologic conditions, leading to a significant increase in volume. The results of our gel swelling experiments were notable for two reasons. First, the increase in relative wet weight (0%) for OMNCL hydrogels is considerably lower than many experimental and clinically approved PEG-based hydrogels. For example, studies of PEG based hydrogels cross-linked via amide or thioester bonds report increasing relative wet weight values of 50%[25] to 400%[26] within the first 24 hours. In some cases, swelling of implanted materials may lead to complications such as nerve compression[27-31] or other serious problems requiring intervention.[32] Secondly, the swelling experiments provided important evidence of the latent formation of disulfide bonds, and insight into the mechanical consequences of this secondary cross-linking mechanism. Exposure of OMNCL gels to reducing agent resulted in an increase in swelling that was reversible upon removal of reducing agent, implying the formation of disulfide bonds within the gel network. This can be understood to be a result of the S-to-N acyl rearrangement step that releases the thiol side chain of Cys, which then becomes available for disulfide bond formation with other network-bound thiols. Through comparison of the kinetics of the OMNCL reaction (FIGS. 6A, B) and the swelling results (FIG. 15), we surmised that the reduction in swelling observed after about 5 h results from disulfide bond formation. Thus, we conclude that the hydrogels form initially by OMNCL and are later further cross-linked through the formation of disulfide bonds.

Figure 18:
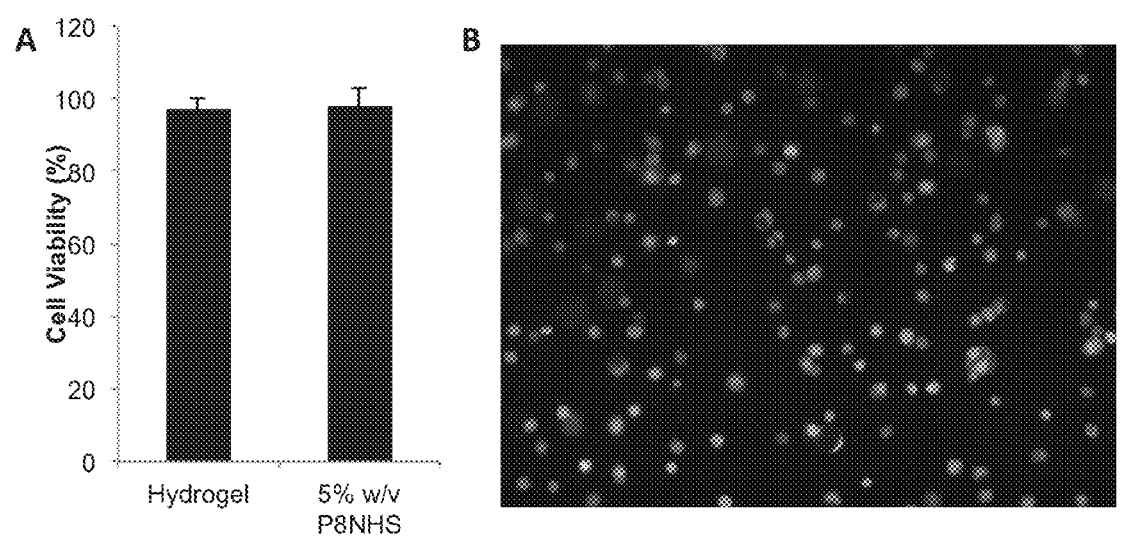
FIG. 18. In vitro cytocompatibility of OMNCL hydrogels. (A) Quantitative analysis of 3T3 fibroblast viability after 24 hours in conditioned medium, conducted in accordance with ISO standards 10993-05 and 10993-12. Cell culture medium included either extract from P8NHS/P8Cys hydrogel or 5% w/v P8NHS. (B) 3T3 fibroblasts encapsulated in OMNCL hydrogels and stained with calcein AM (green, live cells) and ethidium homodimer-1 (red, dead cells). Image analysis indicated 87±7% of cells remained viable after 24 hours of encapsulation.
Figure 19:
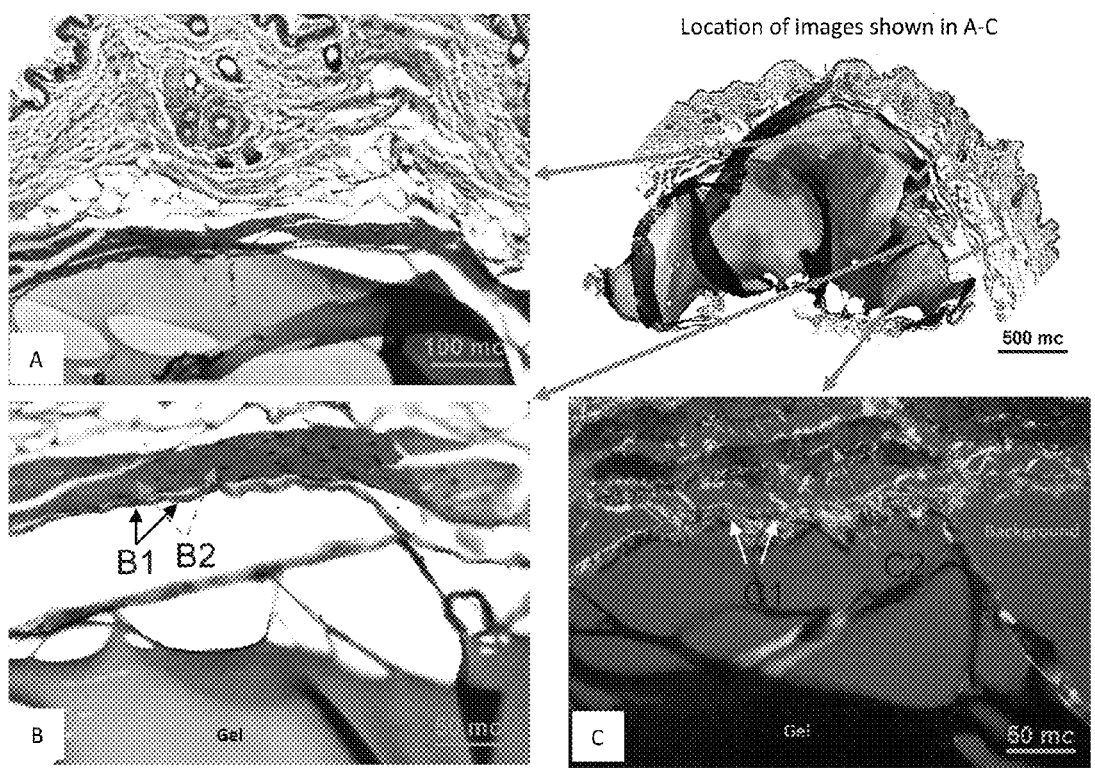
FIG. 19. In vivo subcutaneous characterization of OMNCL hydrogel. (A) H&E stained tissue section at 20× magnification with gel associated with the outer skin. The gel is stained blue and surrounding tissue stained blue and red (an overview of the skin-gel injection area is shown on the right at 4× magnification). (B) H&E stained tissue section at 40× magnification from sequentially obtained tissue sections, showing the gel at the bottom, subtle fibrous capsule (B1) and supra-capsular muscle layer (B2). (C) Picro-Sirius Red stained section (40× magnification) obtained from the same area as (B). Hydrogel is at the bottom; the capsule surrounding the hydrogel is a bright-red fibrous structure (C1) and muscle mass shown in brown-red (C2). The scale bars indicate length in micrometers (mc).

Our in vitro cell experiments demonstrated low cytotoxicity of OMNCL hydrogel extracts and high viability of encapsulated cells (FIG. 18). This led us to undertake an initial in vivo evaluation of OMNCL hydrogels in a subcutaneous implant model. Gels were formed by injection of precursor solutions and then evaluated at 6 weeks. Histological sections of explants showed low-level acute inflammatory response to implanted gels and deposition of a thin fibrous capsule surrounding the implant (FIG. 19). These findings confirm the potential of OMNCL hydrogels for in vivo applications.

Activated ester PEG polymers are currently approved by the FDA in the form of the medical sealants DuraSeal™ and COSEAL™. An important distinction between these existing materials and our OMNCL hydrogels relates to the pH range of the cross-linking reaction. Both DuraSeal™ and COSEAL™ are deployed at highly alkaline pH (typically pH 9-10),[33] whereas the OMNCL hydrogels reported here are capable of rapid gel formation at neutral pH. In our studies, PEG was chosen as the backbone for both components because it is non-cytotoxic and has demonstrated favorable results in previous in vivo studies. PEG is also attractive as a simple platform for quantitative NMR studies and is amenable towards chemical modification. However, it is important to note that the OMNCL hydrogel chemistry described here can be easily adapted for use with other suitable polymer platforms.

In summary, we have detailed the synthesis and characterization of a two-component hydrogel formulation that sets rapidly at physiologic pH and ionic strength in the absence of catalysts or other additives. The cross-linking mechanism was revealed by NMR studies to be primarily OMNCL, proceeding by thiol capture to form a thioester intermediate followed by a S-to-N acyl rearrangement to generate amide cross-links. OMNCL hydrogels exhibit attractive mechanical properties that include high compressive moduli and good adhesion to tissue, and low equilibrium swelling due to the latent formation of secondary disulfide cross-links. The biological performance of OMNCL hydrogels was assessed, showing high in vitro cytocompatibility and low acute inflammatory response in vivo. OMNCL hydrogels represent attractive candidates for in vivo applications such as wound repair and sealing, drug delivery, and tissue engineering.

Example 25

Synthesis of Catechol-Containing Precursors

Figure 24:
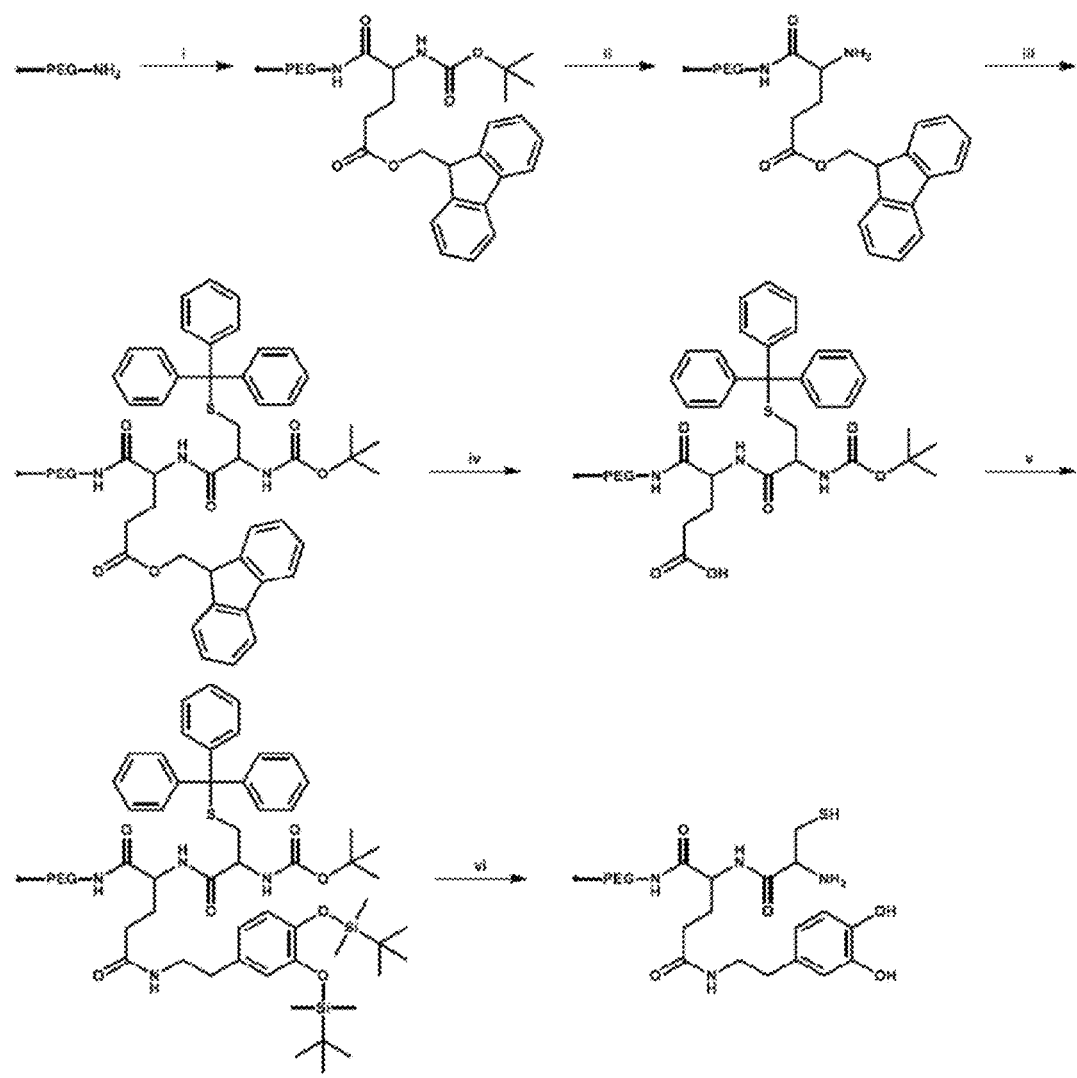
FIG. 24. A scheme for the synthesis of catechol-containing PEG precursor for incorporation into a hydrogel through reaction with PEG-NHS polymers.

This example discloses a reaction scheme for synthesizing catechol-containing PEG precursors. Such precursors can be incorporated into hydrogels through reaction with PEG-NHS polymers through the cross-linking mechanism disclosed herein. The catechol modification introduces another crosslinking moiety and facilitates self healing properties in the resulting hydrogel. The reaction scheme is illustrated in detail in FIG. 24.

Step (i).

Dissolve Boc-L-Glu(OFm)—OH (4 mol. eq. relative to —NH$_2$) in DMF (2 mL/g PEG). Dissolve BOP (4 mol. eq. relative to —NH$_2$). Add DIEA (4 mol. eq. relative to —NH$_2$) dropwise and react for 5 min. In a new DMF solution (2 mL/g PEG), dissolve PEG-NH$_2$. Combine two solutions of DMF and react overnight at room temperature. Ether precipitation. Methanol precipitation. Dry on vacuum line.

Step (ii).

Dissolve PEG-Glu(OFm)—NH-Boc in 30% (v/v) TFA in DCM (10 mL/g PEG). Stir for 90 min at room temperature. Rotovap. Ether precipitation. Methanol precipitation. Dry on vacuum line.

Step (iii).

Dissolve Boc-L-Cys(Trt)-OH (4 mol. eq. relative to —NH$_3$TFA) in DMF (2 mL/g PEG). Dissolve BOP (4 mol. eq. relative to —NH$_3$TFA). Add DIEA (4 mol. eq. relative to —NH$_3$TFA) dropwise and react for 5 min. In a new DMF solution (2 mL/g PEG), dissolve PEG-Glu(OFm)—NH$_3$TFA. Add DIEA (1 mol. eq. relative to —NH$_3$TFA) dropwise. Combine two solutions of DMF and react overnight at room temperature. Ether precipitation. Methanol precipitation. Dry on vacuum line.

Step (iv).

Dissolve PEG-Glu(OFm)-Cys(Trt)-NH-Boc in 20% (v/v) piperidine in DCM (10 mL/g PEG). Stir for 2 h at room temperature. Rotovap. Ether precipitation. Methanol precipitation. Dry on vacuum line.

Step (v).

Dissolve PEG-Glu-Cys(Trt)-NH-Boc in 2:1 (v/v) DMF: DCM (10 mL/g PEG). Dissolve TBDMS-protected dopamine (1.2 mol. eq. relative to —COOH). Dissolve HBTU (1.2 mol. eq. relative to —COOH). Add TEA (1.2 mol. eq. relative to —COOH) dropwise. Stir at room temperature for 2 h. Rotovap. Ether precipitation. Methanol precipitation. Dry on vacuum line.

Step (vi).

Dissolve PEG-Glu(DA-TBDMS)-Cys(Trt)-NH-Boc in a deprotection solution (20 mL TFA, 1.2 mL triisopropylsilane, 1.2 mL ethanedithiol per g PEG). Stir for 3 h at room temperature. Rotovap. Ether precipitation. Methanol precipitation. Dry on vacuum line. Dialyze against acidic water (pH approximately 3.5) for 24 h. Dialyze against MilliQ water for approximately 4 h. Freeze and lyophilize.

Example 26

Synthesis of Glutaric Acid-Terminated Tetronic (T4G)

The same procedure used to synthesize P8G was used to synthesize T4G, with the exception that tetronic was used instead of PEG (100% conversion).

Example 27

Synthesis of N-Hydroxysuccinimide (NHS)-Terminated Tetronic (T4G-NHS)

The same procedure used to synthesize P8G-NHS was used to synthesize T4G-NHS, with the exception that T4G was used instead of P8G (80% conversion).

Example 28

Hydrogel Preparation Using T4G-NHS

PBS was used to prepare 15% (w/v) T4G-NHS and 10% (w/v) P8Cys and the two solutions were mixed in a 1:1 (v/v) ratio to form cylindrical 704 hydrogels (5 mm diameter×3.5 mm height).

Example 29

Drug Delivery with T4G-NHS Hydrogels

Figure 25:
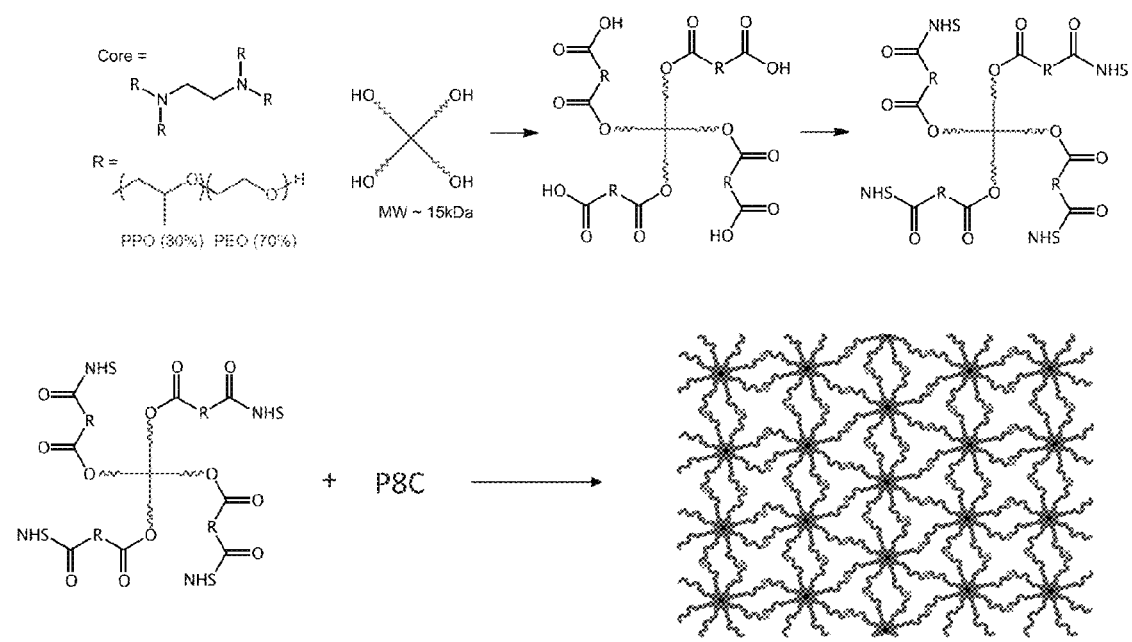
FIG. 25. Hydrogels prepared with T4G-NHS and P8Cys. The variable R group can be varied in a similar fashion as the PEG based polymers (i.e., P8G-NHS, P8GM-NHS, etc.).
Figure 26:
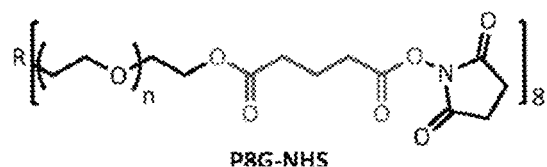
FIG. 26. Structures of first macromonomers comprising an N-Hydroxysuccinimide (NHS) ester group, including A) P8G-NHS, B) P8GG-NHS, C) P8MG-NHS, D) P8S-NHS, E) P8MS-NHS and F) T4G-NHS.
Figure 26:
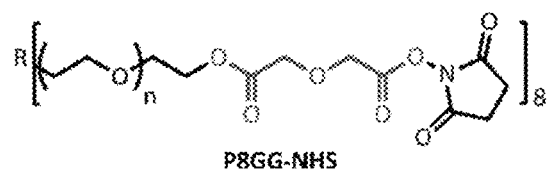
Figure 26:
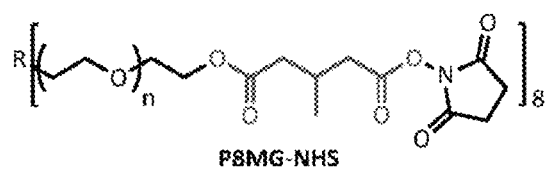
Figure 26:
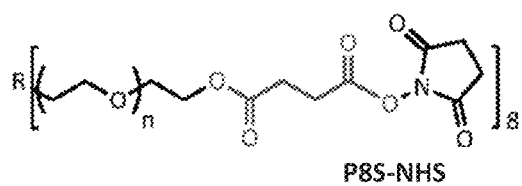
Figure 26:
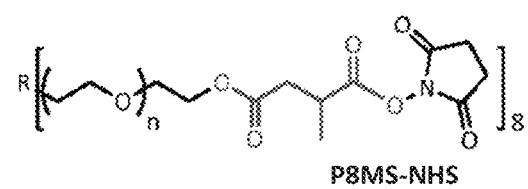
Figure 26:
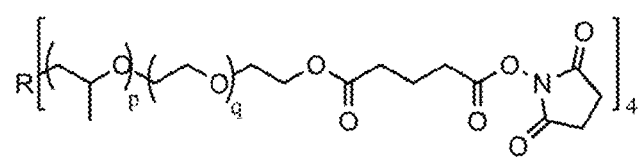

The hydrophobic core of the PPO regions in the T4G-NHS gels (FIG. 25) can be used to load hydrophobic drugs. This method could be used for controlled delivery of hydrophobic drugs.

The above description, attached figures, and below claims are intended to be illustrative and not limiting of this invention. Many themes and variations of this invention will be suggested to one skilled in this and, in light of the disclosure. All such themes and variations are within the contemplation hereof. For instance, while this invention has been described in conjunction with the various exemplary embodiments outlined above and in the below claims, various alternatives, modifications, variations, improvements, and/or substantial equivalents, whether known or that rare or may be presently unforeseen, may become apparent to those having at least ordinary skill in the art. Various changes may be made without departing from the spirit and scope of the invention. Therefore, the invention is intended to embrace all known or later-developed alternatives, modifications, variations, improvements, and/or substantial equivalents of these exemplary embodiments.

REFERENCES (1) Schnolzer et al. *Science* 1992, 256, 221.
(2) Kent, S. B. *Chemical Society reviews* 2009, 38, 338.
(3) Bang et al. *Angew Chem Int Ed Engl* 2004, 43, 2534.
(4) Komarov et al. *ACS chemical biology* 2009, 4, 1029.
(5) Kajihara et al. *Chem Rec* 2010, 10, 80.
(6) Byun et al. *Bioconjugate Chemistry* 2010, 22, 4.
(7) Hu et al. *Biomacromolecules* 2009, 10, 2194.
(8) Jung et al. *Biomaterials* 2008, 29, 2143.
(9) Paramonov et al. *Macromolecules* 2005, 38, 7555.
(10) Ruttekolk et al. *Molecular Pharmacology* 2011, 79, 692.
(11) Ruttekolk et al. *Bioconjugate Chemistry* 2008, 19, 2081.
(12) Su et al. *Biomaterials* 2010, 31, 308.
(13) U.S. Patent Publication Number: US20110262492A1 to Messersmith et al.
(14) Offer, J. *Biopolymers* 2010, 94, 530.
(15) Yuan et al. *Peptide Science* 2010, 94, 373.
(16) Canne et al. *Journal of the American Chemical Society* 1996, 118, 5891.
(17) Warren et al. *Journal of the American Chemical Society* 2004, 126, 6576.
(18) Wan, et al. *Journal of the American Chemical Society* 2008, 130, 15814.
(19) Fang et al. *ChemBioChem* 2010, 11, 1061.
(20) Weissenborn et al. *Chem Commun* (Comb) 2012.
(21) Hu et al. *In Faming Zhuanli Shenqing*; Guangzhou Shengyu Pharmaceutical Science and Technology Co., Ltd: China, 2011, p 20.
(22) Strehin et al. *J. Biomaterials* 2010, 31, 2788.

(23) Jencks et al. *In Handbook of Biochemistry and Molecular Biology;* 4th ed.; Lundblad, R. L., Ed.; CRC Press: 2010, p 595.
(24) Dawson et al. *Science* 1994, 266, 776.
(25) Epstein, N. E. *Spine J* 2010, 10, 1065.
(26) Saunders, et al. *Fertility and sterility* 2009, 91, 560.
(27) Lee et al. *Spine* 2010, 35, E1522.
(28) Mulder et al. *Spine* 2009, 34, E144.
(29) Neuman et al. *Clinical orthopaedics and related research* 2011.
(30) Thavarajah et al. *Spine* 2010, 35, E25.
(31) Parker et al. *J Neurosurg-Pediatr* 2011, 8, 177.
(32) Pace Napoleone et al. *Interactive cardiovascular and thoracic surgery* 2009, 9, 978.
(33) Wallace, et al. *Journal of Biomedical Materials Research* 2001, 58, 545.

We claim:

1. A hydrogel obtained by covalently cross-linking a first macromonomer comprising an N-Hydroxysuccinimide (NHS) ester group with a second macromonomer comprising a N-terminal cysteine group, wherein covalently cross-linking the first and second macromonomers comprises:
   (a) forming an amide bond between the carboxyl carbon of the N-Hydroxysuccinimide (NHS) ester group of the first macromonomer and the primary amine of the N-terminal cysteine group of the second macromonomer to form a third macromonomer, and
   (b) forming a disulfide bond between primary thiol groups on two of the third macromonomers produced in step (a).

2. The hydrogel of claim 1 wherein the hydrogel is biocompatible.

3. The hydrogel of claim 1 wherein the first macromonomer, the second macromonomer, or both, comprise polyethylene glycol.

4. The hydrogel of claim 3, wherein the second macromonomer further comprises a catechol group.

5. The hydrogel of claim 1, wherein the first macromonomer is selected from the group consisting of:

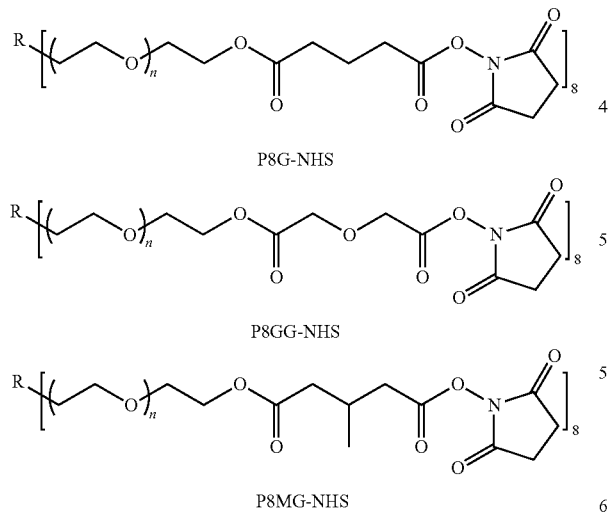

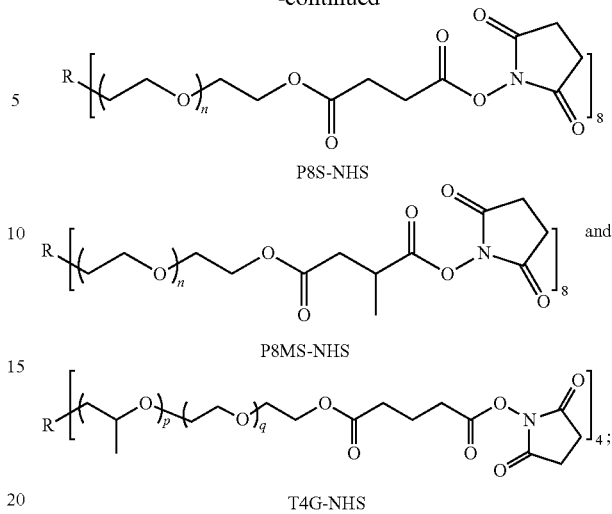

and wherein the second macromonomer comprises the chemical structure:

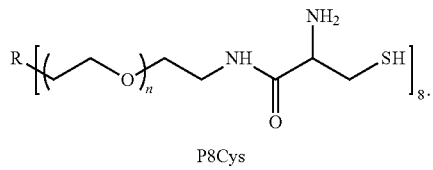

P8Cys

6. The hydrogel of claim 5, wherein each n has a value in the range of from 1 to 201, and wherein each R comprises a hexaglycerin core or a tripentaerythritol core.

7. A method of synthesizing a hydrogel comprising covalently cross-linking an effective amount of a first macromonomer comprising an N-Hydroxysuccinimide (NHS) ester group with an effective amount of a second macromonomer comprising a N-terminal cysteine group, wherein a hydrogel is formed, wherein the step of covalently cross-linking the first and second macromonomers comprises:
   (a) forming an amide bond between the carboxyl carbon of the N-Hydroxysuccinimide (NHS) ester group of the first macromonomer and the primary amine of the N-terminal cysteine group of the second macromonomer to form a third macromonomer, and
   (b) forming a disulfide bond between primary thiol groups on two of the third macromonomers produced in step (a).

8. The method of claim 7, wherein the hydrogel formed is biocompatible.

9. The method of claim 7, wherein the step of covalently cross-linking the first and second macromonomers occurs at physiological pH.

10. The method of claim 7, wherein the first macromonomer, the second macromonomer, or both, comprise polyethylene glycol.

11. The method of claim 7, wherein the second macromonomer further comprises a catechol group.

* * * * *